(12) United States Patent
Baraban et al.

(10) Patent No.: US 9,192,630 B2
(45) Date of Patent: Nov. 24, 2015

(54) TRANSPLANTATION OF NEURAL CELLS

(75) Inventors: Scott C. Baraban, Novato, CA (US); John L. Rubenstein, San Francisco, CA (US); Arturo Alvarez-Buylla, Woodside, CA (US)

(73) Assignee: The Regents of the University of California, Oakland, CA (US)

( * ) Notice: Subject to any disclaimer, the term of this patent is extended or adjusted under 35 U.S.C. 154(b) by 1642 days.

(21) Appl. No.: 12/161,527

(22) PCT Filed: Jan. 18, 2007

(86) PCT No.: PCT/US2007/060715
§ 371 (c)(1),
(2), (4) Date: Oct. 17, 2008

(87) PCT Pub. No.: WO2007/084957
PCT Pub. Date: Jul. 26, 2007

(65) Prior Publication Data
US 2009/0311222 A1   Dec. 17, 2009

Related U.S. Application Data

(60) Provisional application No. 60/760,676, filed on Jan. 20, 2006.

(51) Int. Cl.
*A01N 65/00* (2009.01)
*A01N 63/00* (2006.01)
*A61K 35/30* (2015.01)

(52) U.S. Cl.
CPC ..................... *A61K 35/30* (2013.01)

(58) Field of Classification Search
None
See application file for complete search history.

(56) References Cited

U.S. PATENT DOCUMENTS

| | | | |
|---|---|---|---|
| 6,087,168 A | 7/2000 | Levesque et al. | |
| 7,955,595 B2* | 6/2011 | During et al. | 424/93.2 |
| 2002/0031497 A1 | 3/2002 | Fraser et al. | |
| 2005/0191745 A1* | 9/2005 | Wahlberg et al. | 435/368 |
| 2008/0044901 A1 | 2/2008 | Sasai et al. | |
| 2009/0311222 A1 | 12/2009 | Baraban et al. | |
| 2011/0165129 A1 | 7/2011 | Kriegstein et al. | |
| 2013/0202568 A1 | 8/2013 | Kriegstein et al. | |

FOREIGN PATENT DOCUMENTS

WO   WO2007084957   7/2007

OTHER PUBLICATIONS

Butt et al. (2005) The temporal and spatial origins of cortical interneurons predict their physiological subtype. Neuron 48: 591-604.*
Lavdas et al. (1999) The medial ganglionic eminence gives rise to a population of early neurons in the developing cerebral cortex. The Journal of Neuroscience 99(19): 7881-7888.*
Nery et al. (2002) The caudal ganglionic eminence is a source of distinct cortical and subcortical cell populations. Nature Neuroscience 5(12): 1279-1287.*
Watts (Stereotaxic intrastriatal implantation of human retinal pigment epithelial (hRPE) cells attached to gelatin microcarriers: a potential new cell therapy for Parkinson's disease taken from R. Horowski et al (eds.), Advances in Research on Neurodegeneration, Spring-Verlag/Wien, 2003, pp. 215-227.*
Liu (Nature Biotechnology, 31:440-447.*
Watts, et al., Embryonic donor age and dissection influences striatal graft development and functional integration in a rodent model of Huntington's disease, Experimental Neurology, vol. 163, Issue 1, May 2000, pp. 85-97.
Baraban, et al., Reduction of seizures by transplantation of cortical GABAergic interneuron precursors into Kv1.1 mutant mice, PNAS Sep. 8, 2009 vol. 106 No. 36 15472-15477.
Björklund A, and Lindvall O. Cell replacement therapies for central nervous system disorders. Nat Neurosci. Jun. 2000;3(6):537-44.
Bosch, et al. Induction of GABAergic phenotype in a neural stem cell line for transplantation in an excitotoxic model of Huntington's disease. Exp Neurol. Nov. 2004;190(1):42-58.
Carpenter, et al., In Vitro Expansion of a Multipotent Population of Human Neural Progenitor Cells., Experimental Neurology, vol. 158, Issue 2, Aug. 1999, pp. 265-278.
Chalmers-Redman, et al., In vitro propagation and inducible differentiation of multipotential progenitor cells from human fetal brain., Neuroscience. Feb. 1997;76(4):1121-1128.
Finley, et al., Synapse formation and establishment of neuronal polarity by P19 embryonic carcinoma cells and embryonic stem cells., 1996, Journal of Neuroscience, vol. 16, 1056-1065.
Gernert, et al. Genetically engineered GABA-producing cells demonstrate anticonvulsant effects and long-term transgene expression when transplanted into the central piriform cortex of rats. Exp Neurol. Jul. 2002;176(1):183-92.
Horiguchi, et al., Neural precursor cells derived from human embryonic brain retain regional specificity., Journal of Neuroscience Research, vol. 75, Issue 6, pp. 817-824, Mar. 15, 2004.
Lavdas, et al. The medial ganglionic eminence gives rise to a population of early neurons in the developing cerebral cortex. J Neurosci. Sep. 15, 1999;19(18):7881-8.
Mizuseki, et al. Generation of neural crest-derived peripheral neurons and floor plate cells from mouse and primate embryonic stem cells. PNAS, 2003, vol. 100, No. 10, pp. 5828-5833.
Sussel, et al. Loss of Nkx2.1 homeobox gene function results in a ventral to dorsal molecular respecification within the basal telencephalon: evidence for a transformation of the pallidum into the striatum. Development, (1999) 126, 3359-3370.

(Continued)

*Primary Examiner* — Valarie Bertoglio
(74) *Attorney, Agent, or Firm* — Shweta Chandra; Bozicevic, Field & Francis, LLP

(57) ABSTRACT

Restoration or increase of inhibitory interneuron function in vivo is achieved by transplantation of MGE cells into the brain. Compositions containing MGE cells are provided as are uses to treat various diseases characterised by abnormal inhibitory interneuron function or in cases where increase inhibition may ameliorate neural circuits that are abnormally activated.

19 Claims, 10 Drawing Sheets

(56) References Cited

OTHER PUBLICATIONS

Tabar, et al., Migration and differentiation of neural precursors derived from human embryonic stem cells in the rat brain., Nat Biotechnol. May 2005;23(5):601-606.
Thompson, et al., Embryonic Stem Cell Lines Derived from Human Blastocysts., Science Nov. 6, 1998: vol. 282. No. 5391, pp. 1145-1147.
Thompson. Genetically engineered cells with regulatable GABA production can affect afterdischarges and behavioral seizures after transplantation into the dentate gyrus. Neuroscience. 2005;133(4):1029-37.
Watanabe, et al., Directed differentiation of telencephalic precursors from embryonic stem cells., Nat Neurosci. Mar. 2005;8(3):288-296.
Watanabe, et al. A ROCK inhibitor permits survival of dissociated human embryonic stem cells. Nat Biotechnol. Jun. 2007;25(6):681-6.
Wernig, et al. Functional integration of embryonic stem cell-derived neurons in vivo. J Neurosci. Jun. 2, 2004;24(22):5258-68.
Wichterle, et al. Permissive corridor and diffusible gradients direct medial ganglionic eminence cell migration to the neocortex. Proc Natl Acad Sci U S A. Jan. 21, 2003;100(2):727-32.
Humes, et al. "Stem cells: The Next Therapeutic Frontier.", Trans Am Clin Climatol Assoc. 2005; 116: 167-184.
Kordower, et al., "Functional fetal nigral grafts in a patient with Parkinson's disease: chemoanatomic, ultrastructural, and metabolic studies.", J Comp Neurol. Jun. 24, 1996;370(2):203-30.
Marsala, et al., "Spinal implantation of hNT neurons and neuronal precursors: graft survival and functional effects in rats with ischemic spastic paraplegia"., Eur J Neurosci. Nov. 2004; 20(9):2401-14.
Eaton, et al., "Transplants of neuronal cells bioengineered to synthesize GABA alleviate chronic neuropathic pain.", Cell Transplant. Jan.-Feb. 1999;8(1):87-101 (Abstract Only).
Fine, et al., "Modulation of experimentally induced epilepsy by intracerebral grafts of fetal GABAergic neurons.", Neuropsychologia. 1990;28(6):627-34.
Alvarez-Dolado, et al., Cortical Inhibition Modified by Embryonic Neural Precursors Grafted into the Postnatal Brain, The Journal of Neuroscience, Jul. 12, 2006, 26(28):7380-7389.
Anderson, et al., Distinct cortical migrations from the medial and lateral ganglionic eminences, Development, vol. 128, Issue 3 353-363, Copyright © 2001 by Company of Biologists.
Benninger, et al., Functional Integration of Embryonic Stem Cell-Derived Neurons in Hippocampal Slice Cultures, The Journal of Neuroscience, Aug. 6, 2003, 23(18):7075-7083.
Bjorklund, et al., Neuronal differentiation following transplantation of expanded mouse neurosphere cultures derived from different embryonic forebrain regions, Experimental neurology, 2003, vol. 184, No. 2, pp. 615-635.
Calcagnotto, et al., Inhibitory synaptic transmission in rodents grafted with neuronal precursors from the medial ganglionic eminence, Epilepsia 43 suppl. 7:137 (Abst. 2.030), 2002.
Cobos, et al., Mice lacking Dlx1 show subtype-specific loss of interneurons, reduced inhibition and epilepsy, Nature Neuroscience, vol. 8, No. 8, Aug. 2005, pp. 1059-1067.
Cuevas, et al., Transient maternal hypothyroxinemia at onset of corticogenesis alters tangential migration of medial ganglionic eminence-derived neurons, European journal of neuroscience, 2005, vol. 22, No. 3, pp. 541-551.
Eriksson, et al., Neuronal differentiation following transplantation of expanded mouse neurosphere cultures derived from different embryonic forebrain regions, Experimental neurology, 2003, vol. 184, No. 2, pp. 615-635.

Güttinger, et al., Suppression of kindled seizures by paracrine adenosine release from stem cell-derived brain implants, Epilepsia, 2005, vol. 46, No. 8, pp. 1162-1169.
Jacoby, et al., Long-term survival of fetal porcine lateral ganglionic eminence cells in the hippocampus of rats, J Neurosci Res. Jun. 15, 1999;56(6):581-594.
Loscher, et al., Seizure suppression in kindling epilepsy by grafts of fetal GABAergic neurons in rat substantia nigra, J Neurosci Res. Jan. 15, 1998;51(2):196-209.
Marin, et al., A long, remarkable journey: tangential migration in the telencephalon. Nat Rev Neurosci 2:780-790, 2001.
Nadarajah, et al., Ventricle-directed migration in the developing cerebral cortex, Nat Neurosci—Mar. 1, 2002; 5(3):218-224.
Olsson, et al., Extensive migration and target innervation by striatal precursors after grafting into the neonatal striatum, Neuroscience. Jul. 1997;79(1):57-78.
Olsson, et al., Projection neurons in fetal striatal transplants are predominantly derived from the lateral ganglionic eminence, Neuroscience, vol. 69, Issue 4, Dec. 1995, pp. 1169-1182.
Ross, et al.,Transplantation of M213-2O cells with enhanced GAD67 expression into the inferior colliculus alters audiogenic seizures, Experimental neurology, 2002, vol. 177, No. 1, pp. 338-340.
Ruschenschmidt, et al., Functional properties of ES cell-derived neurons engrafted into the hippocampus of adult normal and chronically epileptic rats, Epilepsia, 2005, vol. 46, pp. 174-183.
The Associated Press, Pig cells transplanted into brain of epilepsy patient, Copyright © 1998 The Standard-Times.
Thompson, et al., Transplants of cells engineered to produce GABA suppress spontaneous seizures, Epilepsia. Jan. 2004;45(1):4-12.
Wernig, et al., Functional Integration of Embryonic Stem Cell-Derived Neurons in Vivo, The Journal of Neuroscience, Jun. 2, 2004, 24(22):5258-5268.
Wicherle, et at., In utero fate mapping reveals distinct migratory pathways and fates of neurons born in the mammalian basal forebrain, Development. Oct. 2001;128(19):3759-3771.
Wicherle, et al., Permissive corridor and diffusible gradients direct medial ganglionic eminence cell migration to the neocortex, PNAS Jan. 21, 2003 vol. 100 No. 2 727-732.
Wicherle, et al.,Young neurons from medial ganglionic eminence disperse in adult and embryonic brain, Nature Neuroscience 2, 461-466 (1999).
Xu, et al., Cortical Interneuron Fate Determination: Diverse Sources for Distinct Subtypes?, Cerebral Cortex, vol. 13, No. 6, 670-676, Jun. 2003.
Xu, et al., Origins of Cortical Interneuron Subtypes, The Journal of Neuroscience, Mar. 17, 2004, 24(11):2612-2622.
de Lanerolle et al., "Hippocampal interneuron loss and plasticity in human temporal lobe epilepsy," Brain Research, pp. 387-395 (1989).
Grothe et al., "The physiological and pharmacological role of basic fibroblast growth factor in the dopaminergic nigrostriatal system," Brain Research Reviews, pp. 80-91 (2007).
Lawrence et al., "Parvalbumin-, calbindin-, and calretinin-immunoreactive hippocampal interneuron density in autism," Acta Neurol Scand, 99-108 (2010).
Ratte et al., "Selective Degeneration and Synaptic Reorganization of Hippocampal Interneurons in a Chronic Model of Temporal Lobe Epilepsy," Adv. Neurol., pp. 69-79 (2006).
Tande et al., "New Striatal dopamine neurons in MPTP-treated macaques result from phenotypic shift and not neurogenesis," Brain, pp. 1194-1200 (2006).

\* cited by examiner

FIGURE 1

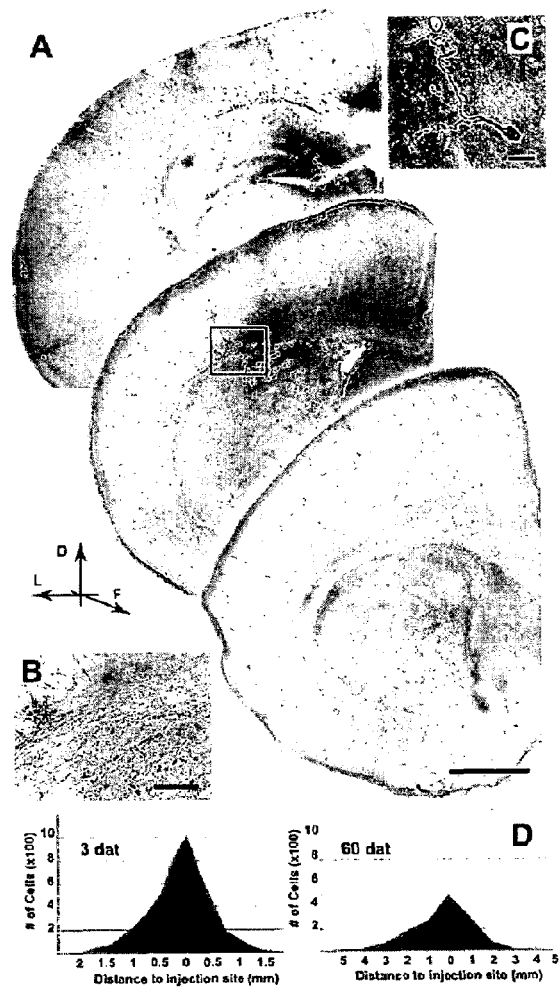

Distribution of MGE derived cells 3 days after transplantation into neocortex and striatum. (A) MGE derived cells were detected by immunohistochemistry against GFP. Serial sections were utilized to determine the position of labelled cells. Notice the wide distribution throughout neocortex, striatum, and hippocampus. (B) High magnification of area in A showing MGE cells moving away from injection site (*). (C) Detail of a typical MGE migrating cell. (D) Distribution of grafted cells 3 and 60 DAT; number of cells/distance of serial sections. Scale bar in A: 1mm; B: 250 µm; D: 25 µm. F, frontal; D, Dorsal; L, Lateral.
47x86mm (600 x 600 DPI)

FIGURE 2

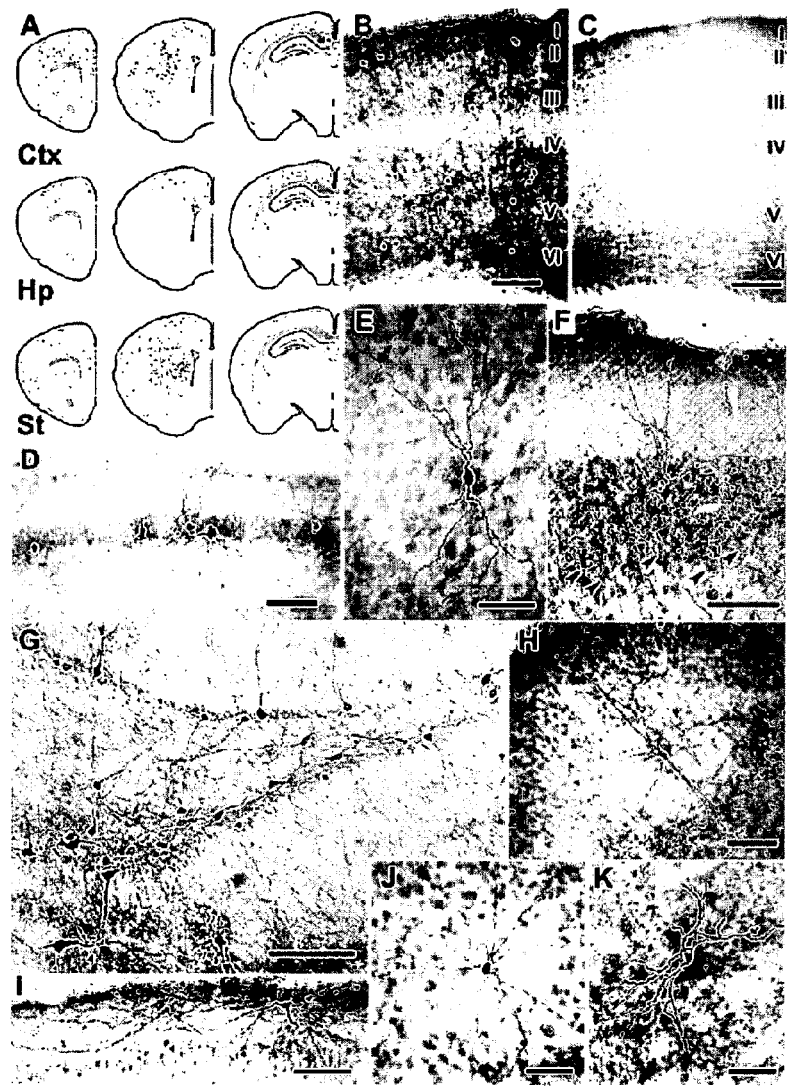

Acquisition and distribution of mature interneuron morphology at 60 DAT. (A) Camera lucida maps indicating the position of MGE graft-derived cells at three rostrocaudal levels after transplantation into neocortex (Ctx), hippocampus (Hp), and striatum (St). (B) Detection of grafted cells by immunohistochemistry against GFP in the ipsilateral somatosensory cortex. Note the wide distribution of grafted cells in multiple cortical layers. Compare the dark background in layers I-II and V of the injected hemisphere (B) versus the contralateral hemisphere (C). (E-K) GFP detection by immunohistochemistry provides a Golgi-like staining of grafted cells. MGE-derived cells in cortex differentiated into neurons presenting typical morphology of interneuron subtypes e.g., bitufted or bipolar cells (E), chandelier cells (F) with synaptic boutons resembling candlesticks Molecular characterization of MGE graft-derived cells in somatosensory (A-F, J-O), and cingulate cortex (G-I), 60 DAT. Immunohistochemical co-localization of grafted GFP+ cells with GABA, Parvalbumin (PV), Calretinin (CR), Somatostatin (SOM), and Neuropeptide-Y (NP-Y). Arrowheads show double positive cells for GFP and specific marker. Scale bar 50 □m for A-O.

FIGURE 5

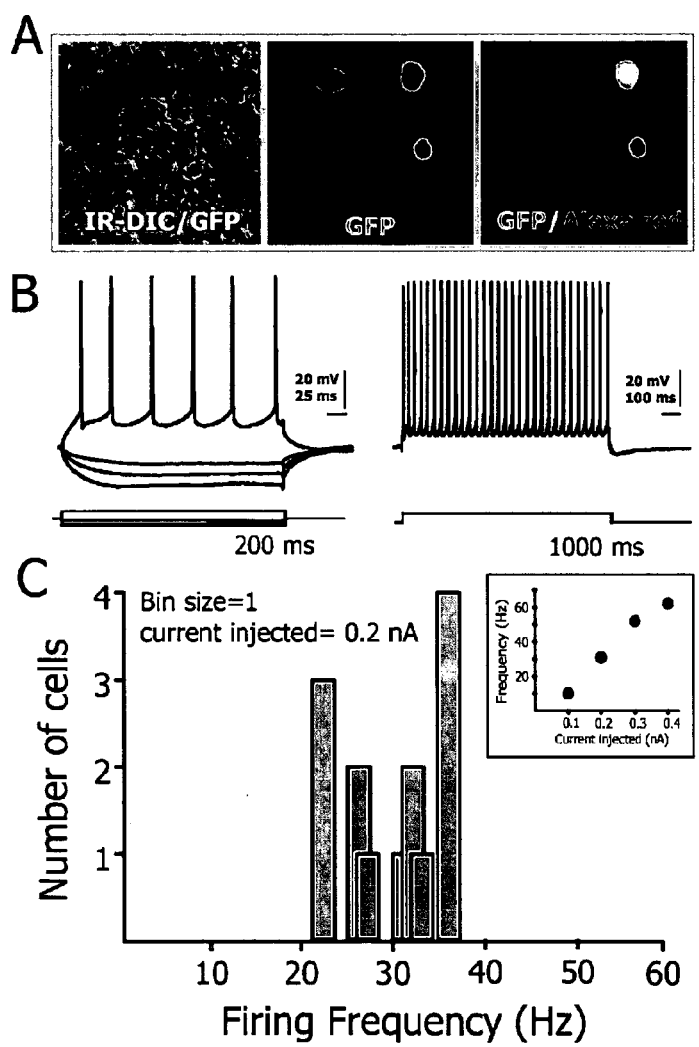

MGE-derived cells exhibit interneuronal firing properties. (A) IR-DIC image overlayed with an epifluorescence image of an acute coronal slice (4 weeks post-grafting) containing GFP+ MGE-derived cells; epifluorescence image at right of a cell filled with Alexa red during the patch recording. (B) Membrane potential of the GFP+ cell shown in panel A recorded under current clamp at the resting potential (~-71 mV). Note the small degree of inward rectification with hyperpolarizing current steps (200 ms) the lack of spike frequency adaptation with long depolarizing current steps (1000 ms) typical of mature cortical interneurons. (C) Graph of firing frequency of recorded GFP+ cells at depolarizing step of 0.2 nA (n = 14). Note the linear frequency-current relationship (inset graph).

FIGURE 6

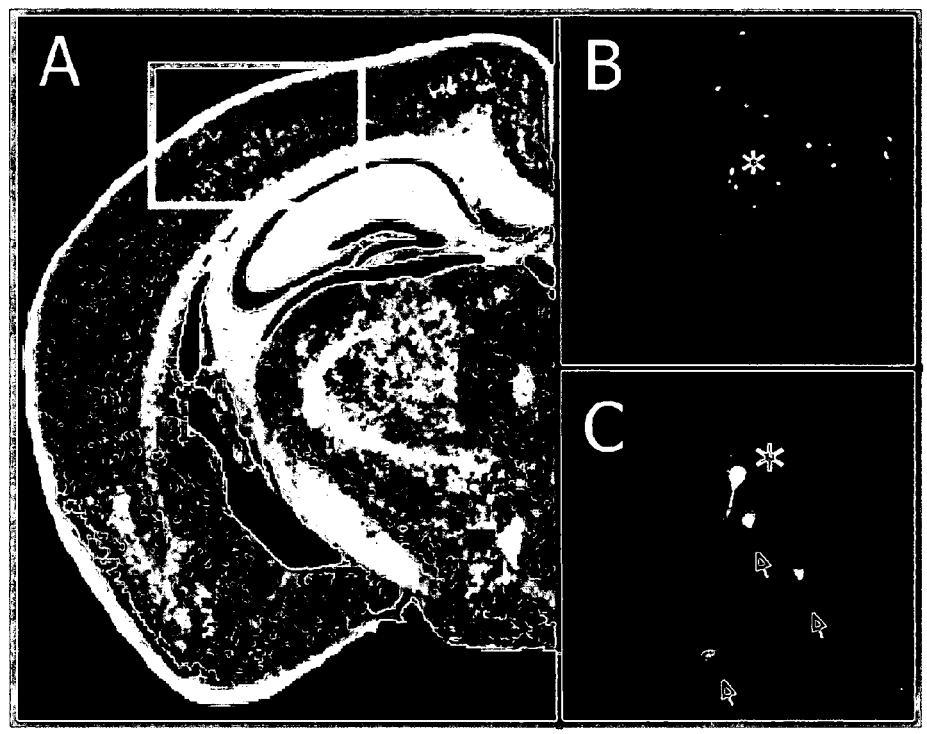

Recording configuration for analysis of inhibitory current in the host brain (A) Left panel shows a representative example of an acute coronal slice. Box indicates region in which electrophysiological recordings were obtained. (B) Panel shows the acute coronal slice with GFP+ cells in Layers I-III visualized under IR-DIC and epifluorescence microscope. A recording was obtained from a pyramidal neuron (asterisk) in the vicinity of GFP+ cells. (C) Panel shows a higher magnification of the recording site with GFP+ MGE cells (green arrows) and a Lucifer yellow filled pyramidal neuron (yellow asterisk).
83x66mm (600 x 600 DPI)

FIGURE 7

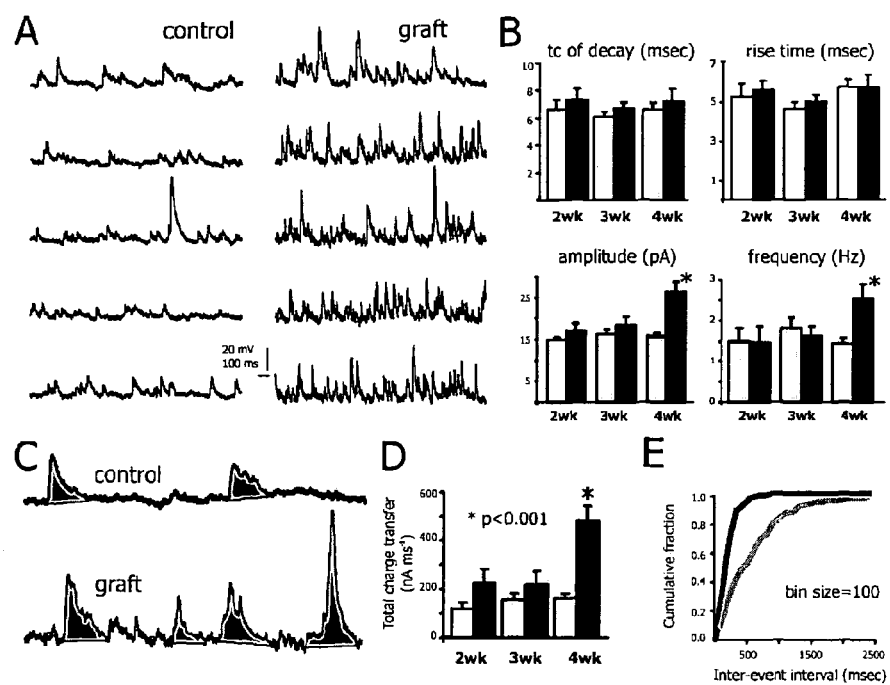

MGE grafted cells alter synaptic function in the host brain. (A) Sample traces of sIPSCs recorded from pyramidal cells (control brain and grafted brain); 4 weeks post-grafting. Note the increase in IPSC amplitude and frequency for grafted animals vs. age-matched controls. (B) Cumulative data plots for all IPSC recordings from control (light gray bars) and grafted (black bars) animals are shown. Recordings were made at 2, 3, and 4 weeks following grafting. Data represent 7-10 cells for each bar; data presented as mean ± S.E.M.; significance taken as $p < 0.05$ using one-way ANOVA. (C) Measurement of the total charge transfer for pyramidal cells from control and grafted brain. Note the significant increase for grafted brains at 4 weeks. (D) Cumulative probability plots of sIPSCs inter-event intervals show higher frequency values for grafted brains ($p < 0.05$)
111x87mm (600 x 600 DPI)

FIGURE 8

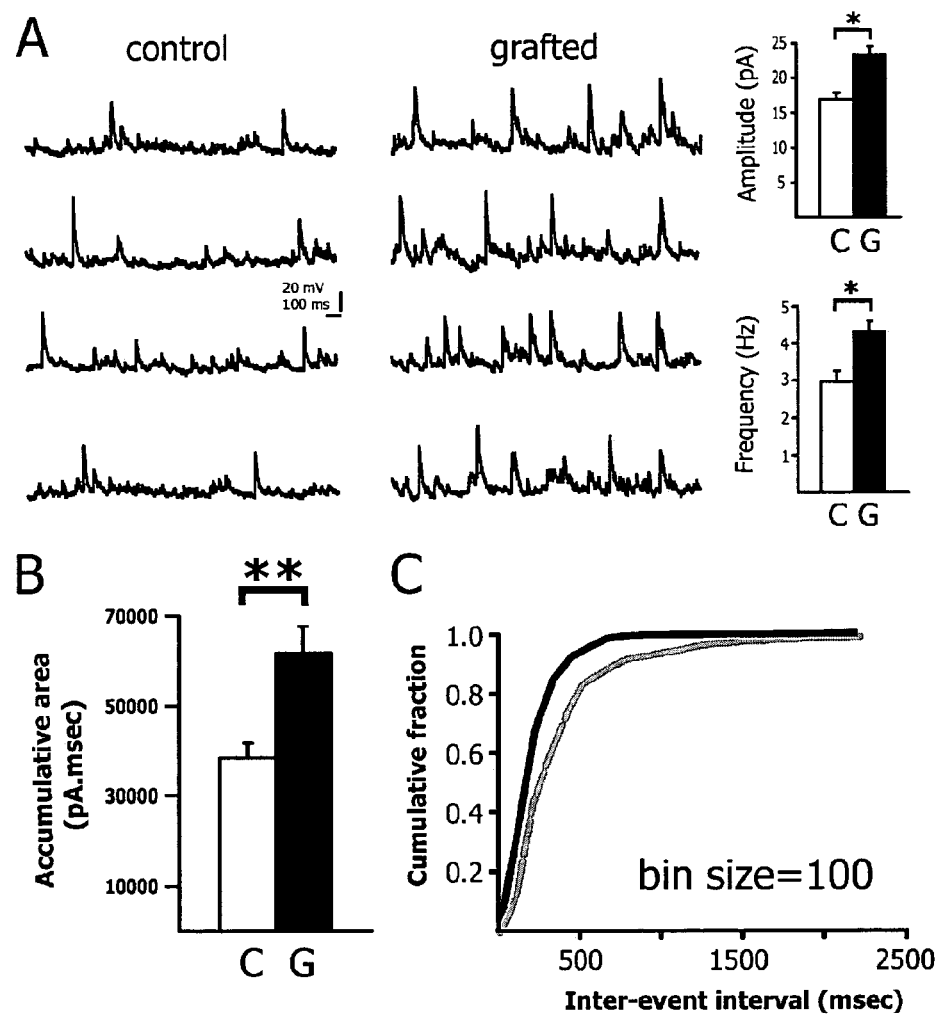

Synaptic inhibitory current is increased in the hippocampus from grafted mice. (A) Spontaneous IPSCs of hippocampal pyramidal cells from control grafted mice with plots of frequency and amplitude of sIPSCs of hippocampal pyramidal cells from control (light gray bars; n = 10) and grafted mice (black bars; n =10). (B) Measurement of the total charge transfer of IPSCs recorded from CA1 hippocampal pyramidal cells from control and grafted brain. Note the significant increase values for grafted brains at 4 weeks. (D) Cumulative probability plots of sIPSCs inter-event intervals shown higher frequency values for grafted brains (p < 0.05). Error bars indicate SEM.; *p < 0.001; ** p < 0.05(ANOVA).
94x104mm (600 x 600 DPI)

FIGURE 9

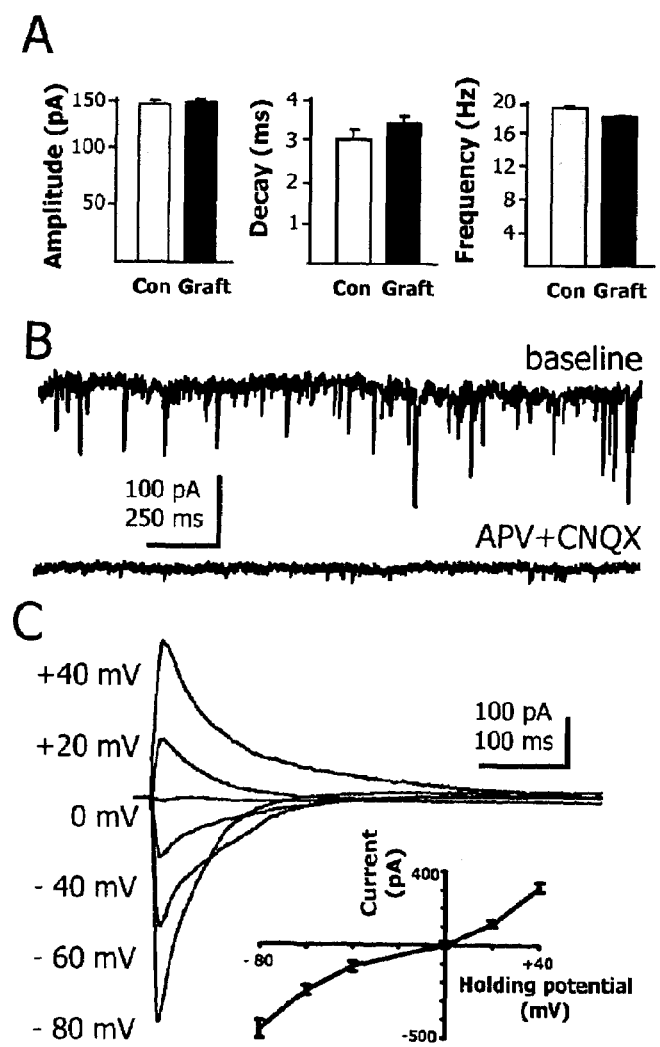

Glutamatergic synaptic excitation is not altered in neocortex and of MGE grafted mice. (A) Plots of all cortical pyramidal cells sampled for spontaneous EPSC data. sEPSC amplitude, decay-time and frequency show no significant difference between controls (light gray bars) and grafted (black bars) brains (B) Representative traces of sEPSCs recorded from a GFP+ grafted cell at 4 weeks post-grafting. sEPSCs were abolished by application of CNQX and APV (bottom trace) (C) Sample of eEPSC recording from GFP+ grafted cells at different holding potentials showing the reversal membrane potential at 0 mV (see inset graph).

FIGURE 10
■ Dlx1$^{-/-}$ without MGE transplantation
□ Dlx1$^{-/-}$ with MGE transplantation
□ Dlx1$^{+/-}$
sIPSCs
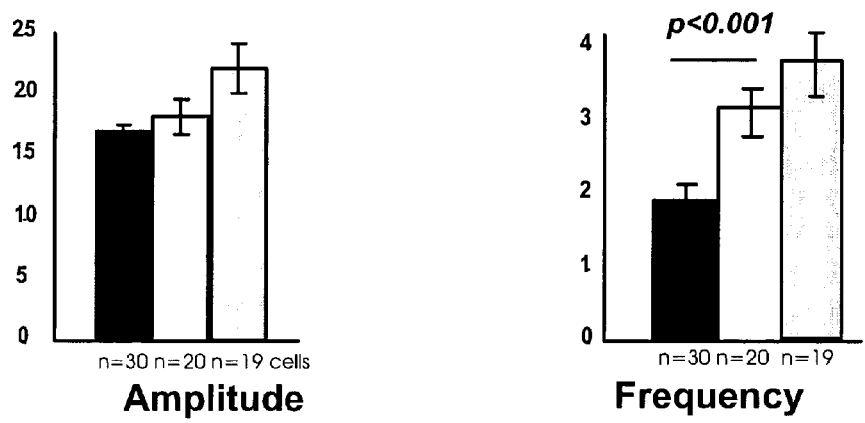
mIPSCs
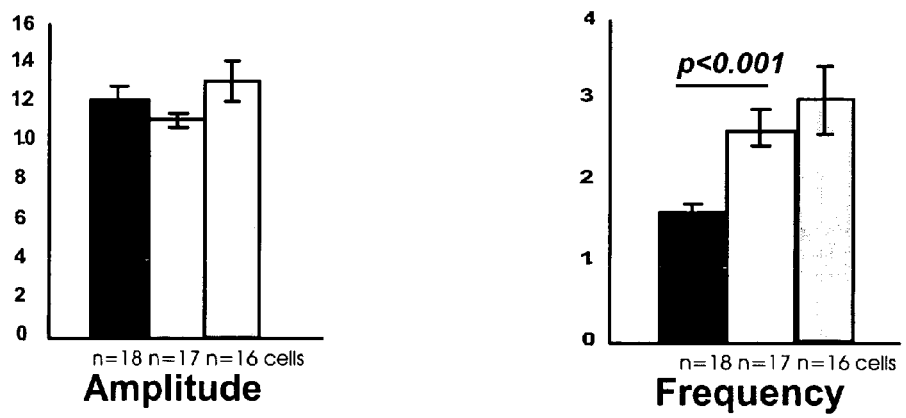
9 Dlx1 ko transplanted mice
7 Dlx1 ko mice without transplantation
8 Dlx1$^{+/-}$

TRANSPLANTATION OF NEURAL CELLS

FIELD

The present invention relates to transplantation of neural cells to increase inhibitory neuron activity in brain. It relates in particular to treatment of disorders that would benefit from increased inhibitory neuron activity—this could include, but is not limited to disease characterized by loss of inhibitory neuron function—and to compositions useful therefor and further relates to treatment of human disease including epilepsy and Parkinson's disease.

BACKGROUND TO THE INVENTION

Many neural disorders are characterised by abnormal inhibitory neuron signalling and, in particular a lack of the neuro-transmitter γ-aminobutyric acid (GABA), secreted by inhibitory neurons. GABA, a metabolite of glutamate, is an inhibitory neurotransmitter which counteracts the effects of excitatory neurotransmitters. Excitatory neurotransmitters (typically acetylcholine, glutamate, or serotonin) open cation channels, causing an influx of $Na^+$ that depolarises the postsynaptic membrane toward the threshold potential for firing an action potential and hence cause the propagation of a signal across the synapse. Inhibitory neurotransmitters, by contrast, open either $Cl^-$ channels or $K^+$ channels, and this suppresses firing by making it harder for excitatory influences to depolarise the postsynaptic membrane.

Abnormal inhibitory function may contribute to symptoms of Parkinson's Disease and is fundamental to the pathology of several other neural disorders including Huntington's Disease, Schizophrenia, autism, chronic pain and many forms of Epilepsy. Epilepsy, in common with most such disorders, has no known cure and is treated with a range of drugs aimed at managing the symptoms. Therefore Epilepsy and its treatment result in a severe degradation of quality of life, measured in days of activity, pain, depression, anxiety, reduced vitality and insufficient sleep or rest (similar to arthritis, heart problems, diabetes, and cancer). Epilepsy affects 50,000,000 people worldwide and sufferers have a mortality rate two to three times higher than that of the general population with the risk of sudden death being 24 times greater. In addition to personal suffering, epilepsy imposes an annual economic burden of $15.5 billion in the USA alone, in associated health care costs and losses in employment, wages, and productivity. Therefore any alternative or new therapy, especially one with the potential to be curative, would have very far reaching benefits.

Research aiming to enhance inhibitory neuron function by cell transplantation has focused on the use of multi-potent cells and immortalised neurons that have been genetically engineered to produce GABA (Bosch et al., (2004) Exp Neurol 190, 42-58; Thompson, (2005) Neuroscience 133, 1029-37).

In order for the grafted cells to effectively reach affected regions and functionally integrate, it is necessary that the cells migrate away from the site of the graft and intermix with the host cells establishing inhibitory synapses with local excitatory neurons. A lack of migratory activity of the transplanted cells has been a flaw of previous attempts to derive new neural tissue from precursor cells, such as in the case of embryonic stem cell (ES)-derived neurons (Wernig et al., (2004) J Neurosci 24, 5258-68; Ruschenschmidt et al., (2005) Epilepsia 46 Suppl 5, 174-83) and genetically engineered GABA-producing cells (Bosch et al., supra.; Thompson, supra). ES-derived cells or other neural precursors transplanted into postnatal brains do not migrate extensively but form clumps of graft-derived cells in, or near, the site of transplantation (Bosch et al., supra; Ruschenschmidt et al., supra; Thompson, supra) and thus their value as a therapy is restricted, since usage would require multiple graft sites and only a limited volume of brain parenchyma can be modified. It is also unlikely that the grafted cells could be adequately positioned to effectively increase inhibition if the position of their cell body is constrained to the site of transplantation.

During development, cells from the medial ganglionic eminence form inhibitory interneurons. Studies on MGE cells are contradictory. One recent study (Olsson M et al. Neuroscience 69(4) 1169-82 (1995)) concluded that MGE cells have a relatively low migratory capacity, compared with other neural precursor cells, when transplanted into a host brain and that they would not be able to cross regions of the brain affected by neural disease, whereas the paper by Butt et al. (Neuron 48, 591-604, 2005) reported rapid migration.

ES cells have been shown to produce differentiated neurons in a host brain and so appear to be an excellent prospect for restoration of inhibitory neuron function in the diseased brain. However, ES-derived transplants also form a heterogenous population of cells—although roughly 14% of ES-derived cells grafted into the postnatal brain express GAD67 (a marker of GABA-containing interneurons), another 44% exhibit a glutaminergic phenotype, and so would be likely to have an excitatory function (the opposite to that desired), and an unknown number are presumably astrocytes (Wernig et al., supra). Also transplantation of ES-derived progenitor cells in order to increase GABAergic activity of the brain is fundamentally flawed, not only because of the limited migratory capacity of the cells, as mentioned above, but also because, following transplantation, formation of tumours is a common problem (Wernig et al., supra; Ruschenschmidt et al., supra).

OBJECTS OF THE INVENTION

An object of the present invention is to provide increased inhibitory neuron function in the brain, and another object is to ameliorate or at least provide an alternative therapy for diseases characterized by abnormal inhibitory interneuron activity or function. In addition an object of particular embodiments is to increase inhibition in cases where inhibitory interneuron function is normal, but excess excitation may cause pathological symptoms. An object of specific embodiments of the invention is to treat disease by transplantation of cells and for transplanted cells or their progeny to disperse through disease-affected areas and differentiate into mature neurons expressing appropriate neurotransmitters or neuropeptides. These cells should functionally integrate and directly influence circuitry in the damaged host brain. Preferably, grafted cells should be able to disperse through the affected area and differentiate into neurons that contribute to restoration (or modulation) of existing neural circuit deficits. As such, transplantation of neuronal precursors can then be used as a therapeutic strategy for brain repair or circuit modification in which increase of inhibitory neuron function is required. These cells can also be used as vehicles to deliver the expression of molecules for a wide range of disorders including, but not limited to, cancer, infectious diseases, neurodegenerative diseases, traumatic brain injury, and psychiatric disorders.

SUMMARY OF THE INVENTION

According to the present invention there is provided a method of increasing inhibitory neuron activity in the host central nervous system in a mammal, comprising transplanting MGE cells into the brain of that mammal. In particular, the method is for modifying inhibition in the brain, such as a diseased brain.

The invention also provides a method of delivery of an inhibitory interneuron into a first portion of a mammalian brain, comprising transplantation of MGE cells into a second portion of the brain, distal from the first.

The invention further provides a method of creating an inhibitory interneuron, comprising obtaining an MGE cell and treating that cell so as to create an inhibitory interneuron with potential for functional integration in the host CNS.

Compositions of the invention are provided, comprising isolated human MGE cells in a carrier, suitable for transplantation into a human brain.

The invention still further provides use of an MGE cell in manufacture of a composition for increasing inhibitory interneuron activity in a mammal.

The invention hence provides methods and compositions to increase inhibitory interneuron function in the central nervous system and can provide methods and compositions and uses for treatment of disease characterised by abnormal inhibition, especially such diseases as epilepsy and in particular such diseases in humans. In addition, the invention hence provides methods and compositions and uses for treatment of disease characterised by abnormal excitation, which can be characteristic of diskinesias or neuropathic pain, and in particular such diseases in humans.

The invention additionally provides in certain embodiments a method to deliver therapeutic molecules for the treatment of disease, specifically by expressing these molecules in transplanted MGE cells so that they are then expressed in the functional interneurons produced.

DETAILED DESCRIPTION OF THE INVENTION

The present invention is based upon the transplantation of MGE cells into adult or immature brain so as to form new, functional inhibitory interneurons that can restore or modify neural circuits. A first aspect of the invention is a method of enhancing inhibition in a mammal, comprising transplanting MGE cells into the brain of that mammal. The method is of use in diseased brain, in which such interneurons have been functionally impaired, damaged or destroyed, and so the invention advantageously provides for restoring inhibitory interneuron function in the brain. Diseases which may benefit from increased inhibitory function in the CNS can thus be treated such as those characterised by abnormal excitatory neuron function.

In use, an MGE cell is transplanted and forms or creates an inhibitory interneuron de novo in the brain. Typically a plurality of cells is used, forming a plurality of interneurons. In examples described in more detail below, these are found to have dispersed from the location of transplantation and to have differentiated from the original MGE cells.

A second aspect of the invention is a method of delivery of an inhibitory interneuron into a first portion of a mammalian brain, comprising transplantation of MGE cells into a second portion of the brain, distal from the first. Migration and subsequent differentiation of the MGE cell delivers the functional interneuron. Lack of inhibitory interneuron circuitry is commonly seen across many areas of diseased brain, and it is an advantage that the invention comprises transplantation into one location from which cells and progeny disperse, providing interneuron populations in many distal locations. It is hence not necessary to transplant cells into multiple loci. The interneuron can be genetically engineered to express a heterologous gene. In an example, the interneurons expressed GFP and other cells of the invention can be modified to express other proteins to be delivered to the brain.

The interneuron can also be genetically engineered to express a heterologous gene of therapeutic value. For example, MGE cells could be used to deliver proteins selected from: proteins for combating CNS malignancies; proteins for treatment of epilepsies, e.g. by modifying specific signalling pathways; proteins for treatment of neurodegenerative disorders, e.g. Alzheimers, including molecules that contribute to the clearance of neurotoxic substances; and proteins for treatment of neuropsychiatric disorders, e.g. autism and schizophrenia.

A further aspect of the invention is a method of creating an inhibitory interneuron, comprising obtaining an MGE cell and treating that cell so as to create an inhibitory interneuron. The inhibitory interneuron is preferably part of a neural circuit in which it provides inhibitory feedback via secretion of inhibitory neurotransmitters such as GABA. A suitable treatment is to transplant the cell into mammalian brain, especially diseased brain.

The invention is of application generally to mammals, and in particular wherein the mammal is selected from the group consisting of mouse, rat, human, livestock animals and domestic animals. Preferably, the mammal is a human and the invention provides compositions containing human cells and methods and uses for treatment of human disease.

MGE cells are described in a number of reports. For use in the present invention MGE cells from a variety of different sources may be used. The cells may be obtained from foetal or embryo brain, for example by dissection of tissue and then dissociation of cells to yield a composition comprising dissociated cells. MGE cells may also be obtained by differentiation of a neural stem cell. Thus a neural stem cell is treated so as to differentiate into an MGE cell. The neural stem cell may be obtained directly from tissue of a patient. It may be obtained by differentiation of a pluripotent cell, such as an ES cell.

In an embodiment of the invention, MGE cells are transplanted into a region of the brain selected from hippocampus, cerebral cortex, subthalamic nuclei, other thalamic or hypothalamic regions, cerebellum, striatum and spinal cord.

Preferably, the method is for treatment of disease and the patient brain being treated comprises one or more lesions, such as a region with damaged or destroyed inhibitory interneurons, the patient typically being a mammal, especially a human, having consequent reduced inhibitory interneuron activity, or abnormal excitatory activity.

In an example set out in more detail below, dissociated MGE cells are injected into the brain, preferably in association with a carrier, this carrier preferably being an air-buffered cell culture media.

Methods described herein are suitable for treatment of a patient afflicted by a disease characterised by inadequate inhibitory interneuron activity or increased excitatory neuron function and such diseases include Epilepsy, Parkinson's disease, Huntington's disease, Schizophrenia and chronic pain.

A further aspect of the invention is a composition, comprising isolated human MGE cells in a carrier, suitable for transplantation into a human brain. The composition can easily be loaded into a syringe for administration to the recipient.

Various carriers are suitable for the purpose, including tissue culture medium. Preferably the carrier would have an appropriate osmolarity and pH in order to maintain the viability of the cells. In a typical administration from about $10^5$ to $10^7$, preferably from about $3 \times 10^5$ to $3 \times 10^6$, cells are used, generally in from 0.5 to 20 µl of medium, and at a concentration of from 5000 to $2\times10^6$ cells/µl, preferably from $5\times10^4$ to $10^6$/µl. It will be appreciated by one of reasonable skill in the art that the number of cells and cell density may be optimized per host (e.g., human) through routine experimentation.

Still further aspects of the invention lie in the use of an MGE cell in manufacture of a composition for enhancing inhibition in a mammal, the composition being preferably for restoring inhibitory interneuron function or counteracting elevated excitatory neural function e.g. for treatment of a disease characterised by inadequate inhibitory interneuron activity or over activity of excitatory neurons such as neuropathic pain. Another aspect is the use described for de novo creation of an inhibitory interneuron, in particular in a human.

Referring to specific embodiments of the invention such as are described in detail below, transplanted cells are MGE cells, or have the characteristic phenotype of MGE cells. Following transplantation, these cells contribute to the inhibitory neuron function of the host brain, integrating into the host's brain whilst not being tumorigenic. The migration is generally found to be fairly rapid, typically 5-10 µm/hour, facilitating distribution of the cells and progeny neurons throughout the brain. This migration allows delivery of interneurons into regions of the brain distinct from the site of transplantation, e.g. transplantation into the cerebral cortex can result in an inhibitory interneuron creation in the hippocampus. Transplanted cells may be tracked following implantation using molecular markers (e.g. GFP).

Transplanted MGE-like precursors form differentiated interneurons in the host's brain, adopting the morphology of inhibitory interneurons, and have been found to have the ability to migrate across the lesions in the brain which can occur in neural disease. Transplanted cells adopt the phenotype of inhibitory interneurons, such that they express molecules characteristic of mature inhibitory neurons, and are found to alter neural function within the host brain, preferably in a permanent manner. Preferably transplanted cells do not form cortical pyramidal neurons and do not increase excitatory neuron activity in the brain, but cause a net increase in inhibitory neuron function in the brain relative to excitatory function. Transplanted cells hence are used to restore inhibitory neural function to normal levels in diseases characterised by a lack of inhibitory neural function or pathological excitation. The cells, after integration into the host brain, receive synaptic inputs. The cells, after integration into the host brain, also receive excitatory inputs.

An advantage of the invention is that, following transplantation of an MGE cell, there is migration of the cell and formation in situ of a functioning inhibitory interneuron. As a result, and referring to the examples subscribed herein, there is enhanced inhibitory interneuron activity in the recipient due to formation of a functional inhibitory interneuron. This interneuron can be a replacement for one lost due to disease or could be an additional interneuron. This interneuron not only receives synaptic inputs but also excitatory inputs. A consequence of the inhibitory outputs, that the cells are capable of producing, is an increase in GABA mediated synaptic events in the vicinity of the MGE cell derived inhibitory neuron.

A further advantage is that the cells produce mature GABA-secreting interneurons in situ and there is no need artificially to modify transplanted cells so as to secrete GABA.

The invention can thus provide treatment for diseases, such as Epilepsy and other diseases discussed herein, where lack of inhibitory interneuron function and consequent over-activity or inadequate regulation of excitatory interneurons forms an underlying element to the disease.

In an example of the invention discussed in more detail below, MGE cells are obtained by mechanical disruption of a dissected portion of foetal and/or embryonic brain. MGE cells can thus be obtained for transplantation into humans. It is preferred that any MGE cell-containing composition is relatively pure in that other contaminating cells are substantially removed. In certain embodiments of the invention the cellular component of the MGE cell-containing composition comprises at least 85%, at least 90%, or at least 95% MGE cells. In some embodiments at least 98% of the cells are MGE cells.

In the art, drug-based therapies are known in which levels of neurotransmitters such GABA in the brain are increased, sometimes leading to a generalised increase in inhibitory activity. A feature of the present invention is that inhibitory interneurons are formed de novo and in situ in the brain, typically forming functional synapses so as to restore neural circuits—in the case, for example, of Epilepsy by restoring normal regulation of neural circuits with formation an inhibitory interneuron. Rather than simply treating a symptom of these diseases, an advantage of the invention is that an underlying cause of the disease is directly addressed. It also provides a method to target inhibition to an area restricted by the migration of grafted cells. This is in contrast to therapies that increase inhibition throughout the nervous system.

DESCRIPTION OF THE DRAWINGS

The invention is now described in the following specific examples, with reference to the accompanying drawings, in which:

FIG. 1 shows MGE cells migrate rapidly following graft and so distribute throughout the host's brain;

FIG. 2 shows MGE cells distributed throughout the host's brain adopt a mature interneuron morphology;

FIG. 5 shows integrated MGE-derived cells function in a manner characteristic of inhibitory interneurons;

FIG. 6 shows recording configuration for analysis of inhibitory current in host brain;

FIG. 7: shows MGE grafted cells alter synaptic function in the host brain;

FIG. 8 shows synaptic inhibitory current is increased in the hippocampus from grafted mice;

FIG. 9 shows glutamatergic synaptic excitation is not altered in neocortex of MGE grafted mice; and FIG. 10 shows cortical brain slices prepared from Dlx mutant mice transplanted with MGE progenitor cells early in development (P0-P2) exhibit a level of inhibition (measured as spontaneous and miniature IPSCs on postsynaptic pyramidal cell targets in regions containing MGE-GFP interneurons) that is comparable to that observed in control Dlx heterozygote mice.

DETAILED DESCRIPTION OF DRAWINGS

Figure 3:
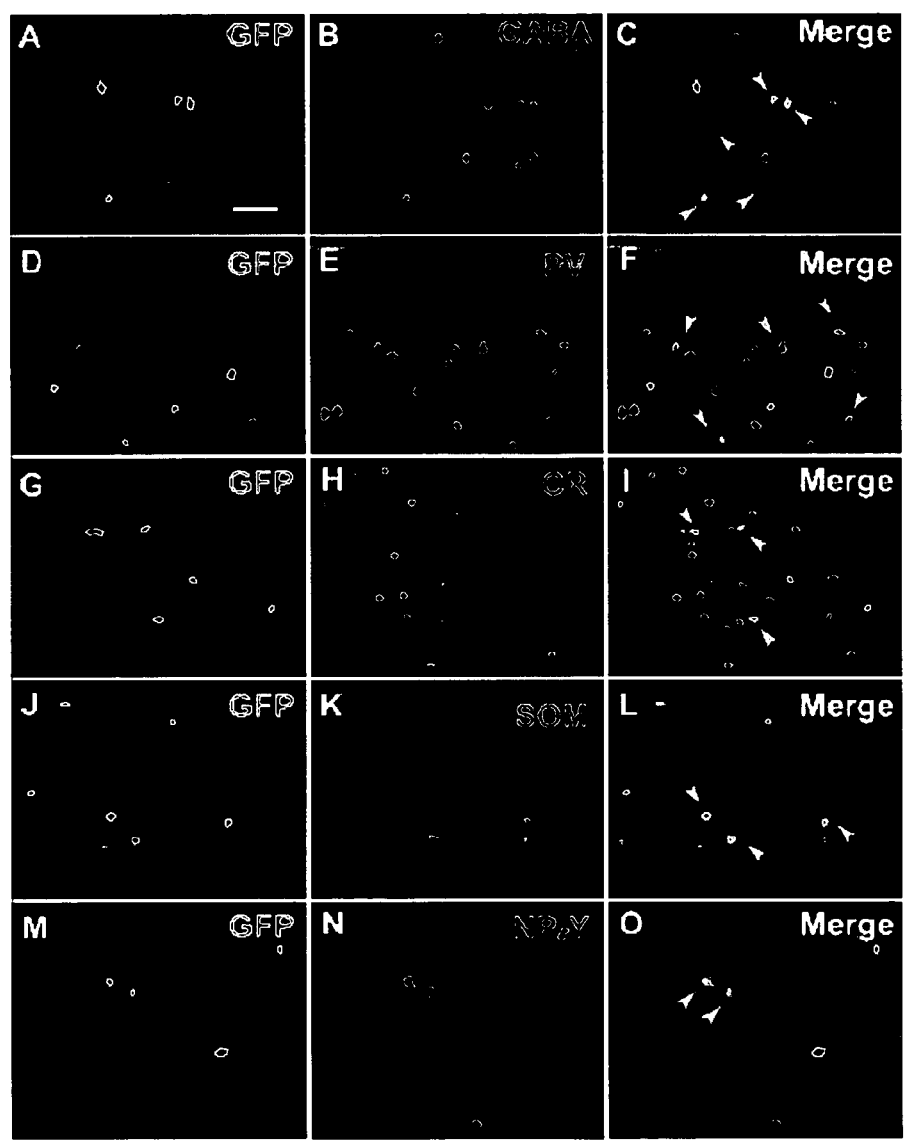
FIG. 3 shows integrated MGE cells in the somatosensory and cingulate cortex express molecules that characterize interneurons.
Figure 4:
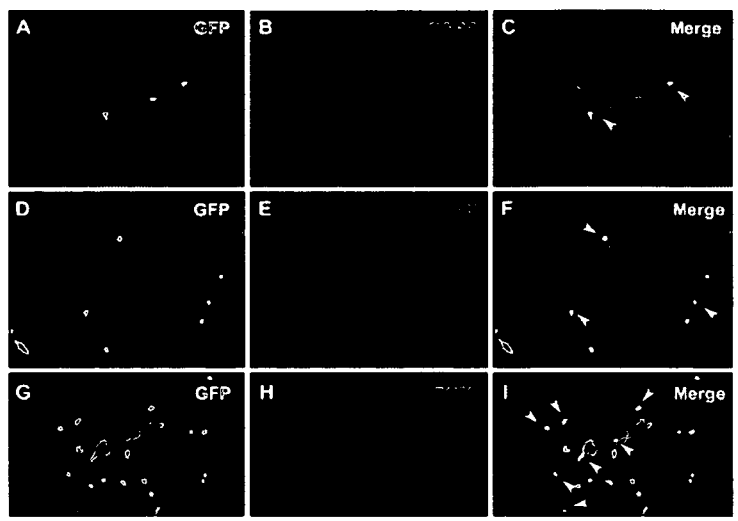
FIG. 4 shows grafted MGE derived cells are present in the dentate gyrus of the hippocampus 60 DAT.

In more detail, FIG. 1 shows distribution of MGE derived cells 3 days after transplantation into neocortex and striatum. (A) MGE derived cells were detected by immunohistochemistry against GFP. Serial sections were utilized to determine the position of labelled cells. Notice the wide distribution throughout neocortex, striatum, and hippocampus. (B) High magnification of area in A showing MGE cells moving away from injection site (*). (C) Detail of a typical MGE migrating cell. (D) Distribution of grafted cells 3 and 60 DAT; number of cells/distance of serial sections. Scale bar in A: 1 mm; B: 250 µm; D: 25 µm. F, frontal; D, Dorsal; L, Lateral;

FIG. 2 shows acquisition and distribution of mature interneuron morphology at 60 DAT. (A) Camera lucida maps indicating the position of MGE graft-derived cells at three rostrocaudal levels after transplantation into neocortex (Ctx), hippocampus (Hp), and striatum (St). (B) Detection of grafted cells by immunohistochemistry against GFP in the ipsilateral somatosensory cortex. Note the wide distribution of grafted cells in multiple cortical layers. Compare the dark background in layers I-II and V of the injected hemisphere (B) versus the contralateral hemisphere (C). (E-K) GFP detection by immunohistochemistry provides a Golgi-like staining of grafted cells. MGE-derived cells in cortex differentiated into neurons presenting typical morphology of interneuron subtypes e.g., bitufted or bipolar cells (E), chandelier cells (F) with synaptic boutons resembling candlesticks (arrowheads), basket cells (H), neurons with small body (I), and multipolar cells (J). In hippocampus, grafted cells accumulated in CA1 (D) and dentate gyrus (G). In striatum, the vast majority of cells differentiated into medium aspiny interneuron (K). Scale bars in B, C, D, F, H and I: 100 µm; E, G, J and K: 50 µm;

FIG. 3 shows molecular characterization of MGE graft-derived cells in somatosensory (A-F, J-O), and cingulate cortex (G-I), 60 DAT. Immunohistochemical co-localization of grafted GFP$^+$ cells with GABA, Parvalbumin (PV), Calretinin (CR), Somatostatin (SOM), and Neuropeptide-Y (NP-Y). Arrowheads show double positive cells for GFP and specific marker. Scale bar 50 µm for A-O;

FIG. 4 shows grafted MGE derived cells in the dentate gyrus of the hippocampus 60 DAT. Immunohistochemical co-localization of MGE derived cells expressing GFP with GABA (A-C), Parvalbumin (PV) (D-F), and Somatostatin (SOM) (G I). Arrowheads show double positive cells. Scale bar 100 µm for A-I;

FIG. 5 shows MGE-derived cells exhibit interneuronal firing properties. (A) IR-DIC image overlayed with an epifluorescence image of an acute coronal slice (4 weeks post-grafting) containing GFP$^+$ MGE-derived cells; epifluorescence image at right of a cell filled with Alexa red during the patch recording. (B) Membrane potential of the GFP$^+$ cell shown in panel A recorded under current clamp at the resting potential (~−71 mV). Note the small degree of inward rectification with hyperpolarizing current steps (200 ms) the lack of spike frequency adaptation with long depolarizing current steps (1000 ms) typical of mature cortical interneurons. (C) Graph of firing frequency of recorded GFP$^+$ cells at depolarizing step of 0.2 nA (n=14). Note the linear frequency-current relationship (inset graph);

FIG. 6 shows recording configuration for analysis of inhibitory current in the host brain (A) Left panel shows a representative example of an acute coronal slice. Box indicates region in which electrophysiological recordings were obtained. (B) Panel shows the acute coronal slice with GFP$^+$ cells in Layers I-III visualized under IR-DIC and epifluorescence microscope. A recording was obtained from a pyramidal neuron (asterisk) in the vicinity of GFP$^+$ cells. (C) Panel shows a higher magnification of the recording site with GFP$^+$ MGE cells (green arrows) and a Lucifer yellow filled pyramidal neuron (yellow asterisk);

FIG. 7 shows MGE grafted cells alter synaptic function in the host brain. (A) Sample traces of sIPSCs recorded from pyramidal cells (control brain and grafted brain); 4 weeks post-grafting. Note the increase in IPSC amplitude and frequency for grafted animals vs. age-matched controls. (B) Cumulative data plots for all IPSC recordings from control (light gray bars) and grafted (black bars) animals are shown. Recordings were made at 2, 3, and 4 weeks following grafting. Data represent 7-10 cells for each bar; data presented as mean±S.E.M.; significance taken as $p<0.05$ using one-way ANOVA. (C, D) Measurement of the total charge transfer for pyramidal cells from control and grafted brain. Note the significant increase for grafted brains at 4 weeks. (E) Cumulative probability plots of sIPSCs inter-event intervals show higher frequency values for grafted brains ($p<0.05$);

FIG. 8 shows synaptic inhibitory current is increased in the hippocampus from grafted mice. (A) Spontaneous IPSCs of hippocampal pyramidal cells from control grafted mice with plots of frequency and amplitude of sIPSCs of hippocampal pyramidal cells from control (light gray bars; n=10) and grafted mice (black bars; n=10). (B) Measurement of the total charge transfer of IPSCs recorded from CA1 hippocampal pyramidal cells from control and grafted brain. Note the significant increase values for grafted brains at 4 weeks. (C) Cumulative probability plots of sIPSCs inter-event intervals shown higher frequency values for grafted brains ($p<0.05$). Error bars indicate SEM; $*p<0.001$; $**p<0.05$ (ANOVA);

FIG. 9 shows glutamatergic synaptic excitation is not altered in neocortex and of MGE grafted mice. (A) Plots of all cortical pyramidal cells sampled for spontaneous EPSC data. sEPSC amplitude, decay-time and frequency show no significant difference between controls (light gray bars) and grafted (black bars) brains (B) Representative traces of sEPSCs recorded from a GFP$^+$ grafted cell at 4 weeks post-grafting. sEPSCs were abolished by application of CNQX and APV (bottom trace) (C) Sample of eEPSC recording from GFP$^+$ grafted cells at different holding potentials showing the reversal membrane potential at 0 mV (see inset graph); and FIG. 10 shows cortical brain slices prepared from Dlx mutant mice transplanted with MGE progenitor cells early in development (P0-P2) exhibit a level of inhibition (measured as spontaneous and miniature IPSCs on postsynaptic pyramidal cell targets in regions containing MGE-GFP interneurons) that is comparable to that observed in control Dlx heterozygote mice.

EXAMPLE 1

MGE cells were transplanted from mice expressing green fluorescent protein (GFP) into the postnatal brain. The time course of migration and differentiation of these neuronal precursors was determined. Also the molecular phenotype of transplanted MGE precursors was analysed using antibodies directed against GABA, somatostatin (SOM) and neuropeptide Y (NPY). Using cortical slices from grafted animals we showed that MGE-GFP neurons exhibit intrinsic firing properties similar to fast-firing basket-type cortical interneurons. Electrophysiological measurements demonstrate that MGE-derived neurons increase the level of GABA-mediated synaptic inhibition, and therefore appear to modify neocortical inhibitory tone.

Materials and Methods

Tissue Dissection and Cell Dissociation. Ventricular and subventricular layers from the anterior part of the medial ganglionic eminence, where a sulcus clearly divides medial and lateral ganglionic eminences, were dissected from E12.5-E13.5 embryonic GFP$^+$ transgenic mice (Hadjantonakis et al., (1998) Mech Dev 76, 79-90). The day when the sperm plug was detected was considered E0.5. Bordering tissue between adjacent regions was discarded during dissection to avoid contamination. Tissue explants were mechanically dissociated by repeated pipetting through 200 µl yellow plastic tip (10-20 times). Dissociated cells were washed with 1 ml of L-15 medium containing DNase I (10-100 µg/ml) and pelleted by centrifugation (2 minutes, 800 g). Cells were resuspended in 4-5 µl of L-15 medium and kept on ice until further use.

Transplantation. Highly concentrated cell suspension (~$10^6$ cells/µl) was front-loaded into beveled glass micropipettes (~50 µm diameter) that were pre-filled with mineral oil and L-15 medium. Micropipettes were connected to a microinjector mounted on a stereotactic apparatus specially adapted for neonatal mice. 3-4 days old CD-1 mice (Charles River) were anesthetized by exposure to −4° C. until pedal reflex was abolished. Anesthesia was maintained by performing surgery on a cold aluminum plate. $5 \times 10^4$ cells/mouse in a 50-100 nl volume were injected using a 45° inclination angle and the following coordinates from Bregma: Striatum (3.3 mm A, 2.5 mm L, 2.6 mm D); Cortex (2.2 mm A, 3.5 mm L, 1.2 mm D); Hippocampus (1.2 mm A, 1.7 mm L, 2.0 mm D). For survival and migration distance estimations, $5 \times 10^3$ cells were grafted in a single point (2.5 mm A, 3.0 mm L, 2.5-1.5 mm D). Grafted pups were returned to their mothers and analyzed after 3 days, 1, 2, 3, 4 weeks and 3 months. All experimental animals were treated in accordance with UCSF Laboratory Animal Research Center guidelines.

Immunostaining. Animals were transcardially perfused with 4% paraformaldehyde at different ages. Brains were removed, postfixed overnight in the same solution, and sectioned coronally (50 µm) using a Vibratome. Floating brain sections were immunostained with the following antibodies: rabbit anti-GABA (1:2500, Sigma), mouse anti-parvalbumin (1:4000, Sigma) and rabbit anti-calretinin (1:4000, Swant Swiss Abs), rat anti-somatostatin (SOM) (1:500, Chemicon), rabbit anti-neuropeptide Y (1:5000, ImmunoStar), and mouse anti-GFP (1:200, Q-Biogene). The following secondary antibodies were used: cy3-conjugated donkey anti-mouse, cy3-conjugated donkey anti-rabbit, cy2-conjugated donkey anti-mouse and biotin-conjugated donkey anti-mouse (1:400, all from Jackson ImmunoResearch, PA). Sections were washed in PBS, blocked for 1 h in PBS containing 10% donkey serum and 0.1% Triton X-100 at room temperature. Sections were then incubated overnight at 4° C. in primary antibodies diluted in PBS containing 10% donkey serum and 0.1% Triton X-100, then were washed three times in PBS and incubated with secondary antibodies for 1-2 h at room temperature in the dark. For GABA immunostaining, Triton X-100 was eliminated from the protocol. Biotinylated secondary antibodies and ABC kit (Vector) were used for peroxidase reaction with diaminobenzidine (DAB).

Cell Counts and Quantification. Quantifications of cell bodies stained with immunohistochemistry or GFP were counted on digitized images obtained with a DFC480 digital camera and IM500/FW4000 image manager software (Leica Microsystems Imaging Solutions, Cambridge, UK) on a DM6000B microscope (Leica Microsystems, Wetzlar, Germany). Survival percentage of grafted cells was estimated counting all GFP$^+$ cells in 10 coronal sections (300 µm apart, 1 section with injection site, 4 forward to the injection, and 5 backward). A representation of cell number vs. distance to injection site was obtained on graph paper. Quantification of area under the graph was estimated as total number of survived cells.

The percentage of grafted GFP$^+$ cells expressing GABA, PV, CR, SOM or NPY after transplantation was calculated in 3 coronal sections through each of the following regions: somatosensory cortex, striatum and hippocampus. For somatosensory each section was 500 µm apart, using stereotaxic coordinates (bregma levels +0.50 and −0.50 mm; Paxinos and Franklin, 2001); striatum sections were 400 µm apart, (bregma levels +1.60 and +0.80 mm); and for hippocampus, sections were 300 µm apart, (bregma levels −1.50 and −2.10 mm). At least 100 GFP$^+$ cells (~50 in cortical layers II-IV, and ~50 in layers V-VI, visualized using DAPI) were analyzed for each marker in each animal. Brains (n=5) were analyzed at 1, 3 and 6 months after transplantation. Statistical analysis was performed using the Student's t-test.

Quantifications of neuronal bodies stained by immunohistochemistry for interneuron markers in grafted and contralateral hemispheres were obtained as follows: In somatosensory cortex, 5 coronal sections (400 µm apart) per mouse between septum (bregma level +0.75 mm) and dorsal hippocampus (bregma level −1.25 mm) were selected. A 1 mm strip of cortex from the white matter to pial surface was analyzed in each section (1.2 mm$^2$ each). In hippocampus, the numbers of positive interneurons in the hilus and CA1 areas were determined in 3 coronal sections (300 µm apart, between bregma levels −1.50 and −2.10 mm) per mouse. In striatum, positive cells were counted in 3 coronal sections (400 µm apart, between bregma levels +1.60 and +0.80 mm) per mouse. Brains from at least 5 different grafted mice were counted and averaged. To compare results between grafted and contralateral hemisphere statistical analysis using the Student's t-test was applied and contralateral results were referred as 100%. Results are presented as mean±SEM. Significance level was taken as $p<0.05$.

Electrophysiology. Acute tissue slices were prepared from male or female CD-1 mice 2, 3, and 4 weeks after grafted with MGE cells or saline (control) as previous described (Calcagnotto et al., (2002) J Neurosci 22, 7596-605). Whole-cell recordings were obtained from visually identified neurons (pyramidal cells and GFP$^+$ cells) using an infrared differential interference contrast (IR-DIC) video microscopy system and epifluorescence microscopy (Molecular Devices). Intracellular patch pipette solution used for whole-cell voltage-clamp recordings to study inhibitory postsynaptic current (IPSC) contained (in mM) 120 Cs-gluconate, 10 HEPES, 11 EGTA, 11 CsCl$_2$, 1 MgCl$_2$, 1.25 QX314, 2 Na$_2$-ATP, 0.5 Na$_2$-GTP, (pH 7.25; 285-290 mOsm); for excitatory postsynaptic current (EPSC) solution contained (in mM) 135 CsCl$_2$, 10 NaCl, 2 MgCl$_2$, 10 HEPES, 10 EGTA, 2 Na$_2$ATP, 0.2 Na$_2$GTP, and 1.25 QX-314, adjusted to pH 7.2 with CsOH (285-290 mOsm). To isolate GABAergic currents, slices were perfused with nACSF containing 20 µM 6-ciano-7-dinitroquinoxaline-2,3-dione (CNQX) and 50 µM d-(−)-2-amino-5-phosphonovaleric acid (D-APV) and IPSCs were recorded at a holding potential of 0 mV; for excitatory postsynaptic currents (EPSC), slices were perfused with nACSF containing 10 µM bicuculline methiodide (BMI) and recorded currents at a holding potential of −75 mV unless otherwise noted. Miniature inhibitory synaptic currents (mIPSCs) were recorded in nACSF containing 1 µM tetrodotoxin (TTX). IPSCs/EPSCs were recorded on "aged-matched" pyramidal neurons (MGE graft-derived or sham-operated) either in the same slice or in a different one. Age-matched refers to slices obtained from mice within a three day time period. Evoked currents were elicited using a monopolar electrode placed in the white matter. Pyramidal cells were filled with biocytin and analyzed post hoc. To study the intrinsic firing properties of GFP$^+$ cells in current-clamp intracellular patch pipette solution contained (in mM) 120 KMeGluconate, 10 KCl, 1 MgCl$_2$, 0.025 CaCl$_2$, 10 HEPES, 0.2 EGTA, 2 Mg-ATP, 0.2 Na-GTP, pH 7.2, (285-290 mOsm). Cells were depolarized and hyperpolarized, via direct current injection (5-1000 ms, duration); cells were filled with Alexa red and analyzed post hoc. Voltage and current were recorded with an Axopatch 1D amplifier (Axon Instruments), and monitored with an oscilloscope and with pClamp 8.2 software (Axon Instruments), running on a PC Pentium computer (Dell Computer Company, Round Rock, Tex.). Whole-cell voltage-clamp data were low-pass filtered at 1 kHz (−3 dB, 8-pole Bessel), digitally sampled at 10 kHz. Whole-cell access resistance was carefully monitored throughout the recording and cells were rejected if values changed by more than 25% (or exceeded 20 MΩ); only recordings with stable series resistance of <20 MΩ were used for analysis (Mini Analysis 5.6.28 software; Synaptosoft, Decatur, Ga.). Results are presented as the mean±SEM. To compare results between different cell types, we used a one-way ANOVA with significance level of $p<0.05$.

Results

Embryonic MGE Cells Grafted in Juvenile Brain Rapidly Disperse Long Distances. To establish an efficient method for the transplantation and functional assessment of MGE progenitors in a host brain, the MGE was dissected from transgenic E12.5-E13.5 mice expressing green fluorescent protein (GFP) (Hadjantonakis et al., supra) GFP expression was used to track the migration and differentiation of grafted cells in live or fixed tissue. After mechanical dissociation, GFP$^+$ MGE cells were loaded into a glass micropipette and grafted into the neocortex and dorsal striatum in the brain of postnatal day 3 or 4 (P3-P4) mice (Lois and Alvarez-Buylla, (1994) Science 264, 1145-8). Host animals were then sacrificed at 3 days, 1, 2, 3 and 4 weeks post-grafting. Representative examples of the injection sites and post-migratory behaviors of GFP$^+$ cells are shown in FIGS. 1A and 2A.

Three days after transplantation (DAT) many GFP$^+$ cells had migrated away from the injection site (FIG. 1B) into most of the neocortex, striatum and hippocampus (FIG. 1A). Survival rate of grafted cells at this time point was 38.9±7.3% (n=10). At 3 DAT most GFP$^+$ cells had the typical morphology of tangentially migrating interneurons, with a small-elongated cell soma and a forked leading process (FIG. 1C). GFP$^+$ cells spread extensively around the injection site in all directions. Grafted cells covered a linear distance of 336±82 μm/day (n=20), with a maximum of 525 μm/day, analyzed 3 DAT; this speed of migration is greater than reported in adults (~120 μm/day) and similar to that measured in vitro (280 μm/day on matrigel) (Wichterle et al., (1999) Nat Neurosci 2, 461-6). A representation of cell number versus migration distances at 3 DAT results in a bell-shape curve (FIG. 1D). These data suggest that cells did not have a strong preference for a particular migratory route and disperse in all directions from the injection site.

Differentiation of Grafted MGE Cells in the Host Brain. Analysis of grafted brains 7 DAT revealed a widespread distribution of GFP$^+$ MGE cells. At 7 DAT, most grafted cells no longer exhibited a migratory morphology; instead they had multiple processes and some cells had a thin and longer axon-like process (data not shown). This indicates that initiation of differentiation of grafted MGE-derived neuronal precursors occurs between three and seven days after transplantation.

Fourteen and 21 DAT, cells acquired progressively a more mature morphology, showing larger and more elaborated dendritic trees with longer axons. At 30 DAT, some GFP$^+$ cells were more than 5 mm away from injection site; their distribution was similar to that found at 3 DAT (FIGS. 1C & 2A). However, the survival percentage was reduced to 19.9±3.9% (n=10). A similar level of survival, 21.2±4.1% (n=10), was observed at 90 DAT. The morphology of the grafted cells was studied following GFP immunohistochemistry, which provides Golgi-like staining. Two months after transplantation, GFP$^+$ cells had elaborate dendritic trees extending profusely through cortical layers (FIG. 2). Axons and their presynaptic terminals could also be visualized (FIGS. 2B-C). Thus grafted cells appeared to complete their differentiation into functionally integrated interneurons within one month after transplantation.

MGE-derived cells in the cortex differentiated into neurons with morphologies of at least five different interneuron subtypes e.g., bitufted or bipolar cells, chandelier cells, basket cells, neurons with small body, and multipolar cells (FIG. 2). For instance, some neurons displayed synaptic buttons resembling arrays of candlesticks, suggesting that they differentiated into chandelier cells (FIGS. 2B, E, F, H, I, J). In contrast, grafted cells in the striatum differentiate primarily to medium aspiny interneurons (FIG. 2K), and in the hippocampus to interneurons with morphologies typical for this region (basket, axo-axonic, and bistratified cells) (FIGS. 2D & G). None of the MGE-derived neurons exhibited morphological features of cortical pyramidal neurons e.g., triangular cell soma extending a thick spiny apical dendrite. Some immature oligodendrocytes were always noted around the injection site; especially close to the corpus callosum, and occasionally in the cortex where they were radially aligned (data not shown). GFP$^+$ cells with an astrocytic morphology were not observed. Therefore, the MGE cells that we grafted are primarily committed to an interneuronal lineage.

MGE-derived Cells Exhibit Molecular Properties of Cortical Interneurons. Recent studies suggest that MGE progenitors are the principal source of cortical GABAergic interneurons (Lavdas et al., (1999) J Neurosci 19, 7881-8; Sussel et al., (1999) Development 126, 3359-70; Anderson et al., (2001) Development 128, 353-63; Wichterle et al., (2001) Development 128, 3759-71). Interneurons can be classified into several subtypes based on neurochemical markers, such as $Ca^{2+}$-binding proteins (parvalbumin (PV), calbindin (CB), and calretinin (CR)), neuropeptides (e.g., somatostatin (SOM), neuropeptide Y (NPY), cholecystokinin (CCK), and vasoactive intestinal polypeptide (VIP)) (DeFelipe, (1993) Cereb Cortex 3, 273-89; Kubota et al., (1994) Brain Res 649, 159-73; DeFelipe, (1997) J Chem Neuroanat 14, 1-19; Gonchar and Burkhalter, (1997) Cereb Cortex 7, 347-58; DeFelipe, (2002) Prog Brain Res 136, 215-38), and recording their physiological properties (Freund and Buzsaki, (1996) Hippocampus 6, 347470; Cauli et al., (1997) J Neurosci 17, 3894-906; Gupta et al., (2000) Science 287, 273-8; Klausberger et al., (2003) Nature 421, 844-8). To evaluate the interneuronal phenotype and molecular characteristics of transplanted MGE-GFP cells, we performed a series of immunohistochemical studies 60 DAT. Double-immunofluorescence revealed that approximately 65-70% of cortical GFP$^+$ graft-derived cells express GABA (FIG. 3; Table 1); a comparable level of GFP$^+$ cells were double-labeled with an antibody against GAD67 (~70%; data not shown). Subsets of the GFP$^+$ neurons express NPY, SOM, PV, and CR (FIG. 3; Table 1), at expression levels and in a distribution similar to those of the host interneurons. Interestingly, SOM-expressing neurons were enriched in layers I-II of the cortex, whereas CR positive cells were almost exclusively found in retrosplenial and cingulate cortex. This suggests that local environment contributes to the specification of some interneuron subtypes.

MGE-derived cells were also immunopositive for these neurotransmitters and markers in the striatum and hippocampus (FIG. 4, Table 1). They were distributed in the same areas that usually contain these types of interneurons. GFP$^+$ cells were immuno-negative for antibodies to glial fibrillary acidic protein (GFAP), or choline acetyl transferase (ChAT), indicating that grafted cells did not differentiate into astrocytes or cholinergic neurons.

MGE-derived Cells Exhibit Interneuronal Firing Properties. To assess whether the MGE-derived cells had electrophysiological characteristics of cortical interneurons, GFP+ cells were targeted for whole-cell current-clamp recording at 4 weeks post grafting. Diffusion of Alexa Red from the patch pipette permitted real-time confirmation of cellular recording site (FIG. 5A). If MGE cells mature into an interneuronal phenotype they should exhibit little spike frequency adaptation, which is a hallmark electrical feature of GABAergic interneurons. In current-clamp recordings from fifteen GFP+ cells sampled in cortical layer V, we measured mean values of −70.9±0.9 mV for resting membrane potential (RMP) and 101.4±4.1 MΩ for input resistance ($R_{IN}$). In fourteen GFP+ cells, depolarizing current pulses elicited action potentials (3.0±0.4 ms duration; 69.0±3.3 mV amplitude) and hyperpolarizing current pulses evoked a small degree of "sag" current (FIG. 5B). These intrinsic membrane properties are in the expected range for "mature" non-accommodating cortical interneurons (Markram et al., (2004) Nat Rev Neurosci 5, 793-807). Most importantly, long duration depolarizing pulses (1000 ms) clearly revealed the fast-spiking, little adapting firing activity characteristic of basket-cell cortical interneurons. One cell did not exhibit active firing properties during step depolarisations, but had a RMP of −70 mV and $R_{IN}$ of 100 MΩ. The high firing frequency typical of GFP+ cells sampled is shown in FIG. 5B; frequency-current relationships were linear as previously reported for fast-spiking hippocampal interneurons (FIG. 5C) (Smith et al., (1995) J. Neurophysiol. 74, 650-72).

Transplanted MGE cells Influence Synaptic Function in the Host Animal. To determine whether transplanted MGE precursors functionally integrate in the host brain, a series of in vitro electrophysiological studies were performed. Regions of neocortex containing GFP+ cells were identified under epifluorescence (FIG. 6) and pyramidal neurons in regions surrounded by GFP+ cells were chosen for patch-clamp recording. Recorded cells were filled with Lucifer yellow for post hoc confirmation of cell location and identity (FIG. 6A). Brain slices were prepared at various time-points following transplantation (2, 3 and 4 weeks). Spontaneous IPSCs on pyramidal neurons (FIG. 7A) reflect activation of postsynaptic GABA receptors following action potential-dependent vesicular transmitter release; IPSCs were completely abolished by 10 μM BMI a $GABA_A$ receptor antagonist (data not shown). If a significant number of transplanted MGE cells integrate into the host micro-circuitry as new GABAergic interneurons, we would expect an increase in the overall level of GABA-evoked synaptic events onto native pyramidal neurons. Increments in GABA-, PV- and SOM-expressing neurons were observed in the cortical hemisphere ipsilateral to the injection site when compared to contralateral hemisphere (Table 2). These increments were significant in a 100 μm area around the graft. In concordance with these anatomical observations, there were significant increases in IPSC amplitude and frequency in slices from transplanted animals 4 weeks following surgery. Control cortical slices were obtained from sham-operated mice or from the contralateral cortex of transplanted mice (which lacked GFP+ cells) (FIGS. 7B-C). IPSC frequency and amplitude were also increased in the hippocampus of grafted animals at 4 weeks post-transplantation (FIG. 8). Consistent with an increase in the number of GABA-producing neurons, mIPSC frequencies were also increased in neocortical and hippocampal pyramidal cells 4 weeks after transplantation (cortex: 2.3±0.1 Hz n=4; CA1: 2.4±0.2 Hz, n=3) when compared with controls (cortex: 1.3±0.2 Hz, n=4; CA1: 1.1±0.1 Hz, n=3; p<0.05). A significant enhancement of GABAergic inhibition was not observed at 2 or 3 weeks following transplantation; not surprisingly as histological analysis at these times showed an immature phenotype of grafted cells. Significant changes in IPSC rise time or decay-time constant were not observed at any time-point (FIG. 7B) suggesting that gross alterations in postsynaptic GABA subunit receptor expression do not occur in grafted animals.

To assess the overall level of inhibitory tone in grafted animals, we performed two additional analyses. First, measurement of the total charge transfer (corresponding to total area under the IPSC current over a specified time period) indicated that synaptic inhibition was significantly increased in slices containing GFP+ cells compared to age-matched controls (FIGS. 7C-D). Second, consistent with an enhancement of GABAergic tone, there was a significant increase in the frequency of sIPSCs plotted as a cumulative distribution (FIG. 7E).

To test whether the transplanted MGE cells synapse onto existing interneurons, and thereby modify cortical excitation (through inhibition of interneuron function), EPSCs were analyzed. EPSCs recorded from pyramidal neurons (holding potential of −75 mV) in regions containing GFP+ cells; spontaneous EPSCs were abolished by application of CNQX and APV confirming a role for postsynaptic glutamate receptors. In comparing spontaneous EPSCs recorded on pyramidal cells from MGE transplanted animals (n=4) and controls (n=4) no difference in amplitude, decay-time constant, rise-time or frequency was noted (FIG. 9A). These findings suggest that overall excitatory tone in the host brain is not altered following grafting of MGE precursors. To address whether transplanted neurons receive excitatory synaptic contact from host axons, we next examined evoked and spontaneous EPSCs in GFP+ neurons. GFP+ cells exhibited spontaneous EPSCs that were blocked by CNQX and APV (n=4) (FIG. 9B) and evoked EPSCs with a reversal potential near 0 mV (FIG. 9C). EPSCs exhibited kinetics similar to those expected for "normal" glutamate-mediated synaptic currents. These results confirm an endogenous excitatory excitation of grafted MGE-GFP neurons. Taken together, these data suggest that MGE-derived GFP+ cells function as inhibitory interneurons receiving excitatory input from local pyramidal neurons and integrating into cortical synaptic circuitry of the host brain in such a manner as to selectively modify inhibition.

The example demonstrates that MGE-derived neuronal precursors grafted into the early postnatal brain are capable of long distance dispersion across the neocortex and other areas of the juvenile brain. These cells then acquire morphological, molecular and physiological characteristics of mature GABAergic interneurons. Finally, these grafted MGE-derived cells functionally integrate and significantly impact synaptic inhibition in the host brain. Thus, the present example demonstrates that MGE precursors could be used to modify synaptic circuits in a postnatal brain. An ability of these cells to disperse when transplanted into the neonatal brain is demonstrated, reaching maximum migration distances of 5 mm two months after transplantation. As such, a single injection of MGE precursors could influence a relatively wide area of the host brain, an important aspect when considering the potential clinical usefulness of transplanted cells. The present results show that more than 65% of MGE-derived cells express GABA. Grafted cells also contain SOM and NPY, neuropeptides normally co-localized in subtypes of mature cortical interneurons (DeFelipe, (1993) supra; Kubota et al., supra; DeFelipe, (1997) supra; Gonchar and Burkhalter, supra). We did not detect pyramidal-like neurons or astrocytes that were derived from transplanted MGE cells. Importantly, tumors were never observed in our MGE grafted mice although this is a common problem when ES-derived progenitors are used for transplantation (Wernig et al., supra;

Ruschenschmidt et al., supra). MGE-derived cells sampled in layer V exhibit an "electrical fingerprint" typical of mature GABA-containing interneurons. For example, MGE-GFP cells consistently fired at a high frequency and exhibited very little accommodation. These firing properties are consistent with a classification as non-accommodating basket-cell interneurons and it is likely that further current-clamp sampling of GFP+ cells across other layers of grafted cortex will uncover additional interneuron sub-types. In previous analysis of functional integration, single-cell recordings focused exclusively on demonstrations that transplanted cells receive synaptic input. Here we also demonstrate that transplanted MGE-derived cells receive excitatory synaptic input (see FIG. 6). Moreover, we present evidence that grafted progenitor cells send inhibitory outputs, which impact (in a functionally relevant manner) existing pyramidal neurons. Notably, we found that pyramidal cells in regions containing MGE-derived cells exhibit an increased number of GABA-mediated synaptic events and that GABAergic tone is significantly enhanced in these regions of the host brain. Because MGE-derived cells did not alter excitatory cortical circuitry or differentiate to neurons with a pyramidal-cell phenotype, these findings suggest a method for selective enhancement of inhibitory systems.

Our demonstration that grafted progenitor cells produce functionally integrated GABAergic neurons, even in the presence of endogenous GABAergic neurons, after embryonic stages of neurodevelopment are complete, and in a wide variety of brain regions, suggests that MGE-derived cells could be useful in neurological conditions where increased inhibition would be beneficial e.g., epilepsy or schizophrenia. MGE precursors may also be used to correct levels of activity in deafferented brain regions such as in Parkinson's disease, or in conjunction with their inhibitory function, may be used as cellular vectors to deliver therapeutic molecules to wide regions of the brain.

EXAMPLE 2

Robust Epileptiform Burst Activity is More Difficult to Initiate in Slices Containing MGE Progenitors Attempts are made to elicit epileptiform burst activity in cortical slices having received MGE progenitor cell grafts and control cortical slices that have not received MGE progenitors. It is determined to be more difficult to initiate robust epileptiform burst activity in slices containing MGE progenitors. This finding supports that MGE progenitors migrate and differentiate into functional interneurons in the host brain (and thus increase synaptic inhibition).

Neocortical slices are prepared from wild-type mice with MGE grafts and age-matched controls. Spontaneous seizure activity is initiated in neocortical slices by raising the extracellular level of potassium, in a step-wise fashion, from 3 to 6 to 9 mM $[K^+]_e$. Previous studies in our laboratory (Baraban and Schwartzkroin, Epilepsy Res. 1995 October; 22(2):145-56) and others (Rutecki et al., J. Neurophysiol. 1985 November; 54(5):1363-74; Traynelis and Dingledine, J. Neurophysiol. 1988 January; 59(1):259-76), demonstrate this is an efficient method to induce spontaneous seizure activity and test anticonvulsant drugs in vitro. The "high K" model reliably elicits status-like interictal-like epileptiform activity and is designed to mimic high $[K^+]_e$ observed during clinical seizures. Epileptiform activity is monitored using field recording electrodes placed in outer (Layers IV/V) and inner (Layer II) neocortex. Epileptiform burst discharge amplitude (in mV), duration (in msec) and frequency (in Hz) is used to quantitatively compare bursting between experimental and control animals. A second method to compare interictal "burst intensity" in different $[K^+]_e$ involves the use of a coastline bursting index (CBI) (Korn et al., J. Neurophysiol. 1987 January; 57(1):325-40). CBI is responsive to changes in the number or amplitude of bursts, and it increases when neuronal synchrony, firing frequency or duration changes—thus, it can be considered a sensitive measure of whether integrated MGE progenitors influence seizure activity.

A separate series of identical experiments is performed using the zero-$Mg^{2+}$ acute seizure model. Removal of $Mg^{2+}$ from the extracellular bathing medium releases magnesium blockade of NMDA-type glutamate receptors and initiates epileptiform activity driven by excess synaptic excitation (Mody et al., J. Neurophysiol. 1987 March; 57(3):869-88). Epileptiform activity elicited in slices from grafted mice is compared with age-matched controls. Analysis is performed as described above. Slices are postfixed and immunostained with an antibody to GFP so the number of grafted MGE-GFP+

TABLE 1

| MGE graft derived interneuron subtypes (n = 5) | | | | | |
|---|---|---|---|---|---|
| | GABA | PV | SOM | CR | NPY |
| CORTEX | 68.6 ± 4.8% | 38.3 ± 5.4% | 43.2 ± 3.9% | 1.9 ± 0.6% | 7.8 ± 1.2% |
| | | | 53.1 ± 5.3%[a] | 10.3 ± 1.3%[c] | |
| | | | 33.2 ± 2.4%[b] | | |
| STRIATUM | 50.9 ± 2.6% | 54.9 ± 7.6% | 39.5 ± 4.6% | 6.4 ± 1.9% | 18.0 ± 2.1% |
| HIPPO (DG) | 42.8 ± 2.9% | 33.7 ± 4.7% | 33.8 ± 8.1% | 10.3 ± 1.7% | 13.1 ± 1.9% |

Quantifications were performed in somatosensory cortex except for
[a]Layers I-III of somatosensory cortex,
[b]Layers IV-VI of somatosensory cortex, and
[c]Retrosplenial cortex.
DG; Dentate Gyrus

TABLE 2

| Interneuron increment in transplanted somatosensory cortex | | |
|---|---|---|
| | CORTEX[1] (100 µm) | CORTEX[2] (1200 µm) |
| GABA | 12.1 ± 3.7% (P < 0.01) | 8.4 ± 3.5 (P < 0.01) |
| Pv | 9.8 ± 2.1% (P < 0.01) | 4.8 ± 3.6% (P = 0.23) |
| SOM (I-III) | 16.1 ± 2.8% (P < 0.01) | 12.9 ± 3.6% (P < 0.05) |

Contralateral results were taken as 100%.
[1]Estimation of cell increment 100 µm around of injection site. Quantification was performed in 2 slices 50 µm forward and backward from injection site.
[2]Estimation of cell increment 1200 µm around of injection site. Quantification was performed in 3 slices forward plus 3 slices backward from injection site. Significance (p) was estimated with a T-student test, N = 10.

cells can be assessed. Using these two different mechanisms of action we reliably determine transplanted progenitors exert anticonvulsant action in vitro.

Results: It is determined to be more difficult to initiate robust epileptiform burst activity in slices containing MGE progenitors. This finding supports that MGE progenitors migrate and differentiate into functional interneurons in the host brain (and thus increase synaptic inhibition). A decrease in burst amplitude, duration or frequency or a change in CBI index provides quantitative evidence that integrated MGE progenitors, by increasing inhibition, reduce epileptic hyperexcitability.

EXAMPLE 3

Seizures Are More Difficult to Initiate in Mice Receiving MGE Progenitors.

Following bilateral MGE grafting in wild-type mice (and sham operated controls; young adult P30 and adult P60 ages) EEG electrodes are implanted bilaterally in neocortex and animals monitored with video-EEG. After a 1 wk recovery period, following surgery, animals are injected with kainic acid (KA, a glutamate receptor agonist) at a concentration previously shown to elicit status epilepticus in the mouse e.g., 30-40 mg/kg i.p. (Baraban et al., Brain Res Dev Brain Res. 1997 Sep. 20; 102(2):189-96; Baraban et al., J. Neurosci. 1997 Dec. 1; 17(23):8927-36). In analyzing video-EEG traces following initiation of a KA-induced seizure, the frequency and duration of electrographic seizure events recorded are quantified. Behaviors that accompany these discharges are fully characterized by close examination of the video-EEG recordings using an investigator blind to the status of the animal. Clinician-scientists in the laboratory with significant clinical EEG experience assist in analysis of this data.

A second set of identical experiments are performed using pentylenetetrazole (a GABA antagonist, 15-20 mg/kg i.p.). Similar to slice electrophysiology studies, two separate means of seizure induction are used to adequately assess the ability of MGE progenitors to decrease/inhibit seizure activity.

In all animals, euthanasia and transcardial perfusion are performed at the conclusion of video-EEG experiments. Brains are rapidly removed and fixed in paraformaldehyde for post hoc confirmation of EEG electrode placement. In addition, brains are sectioned and stained for analysis of $GFP^+$ interneurons. These anatomical studies allow us to correlate numbers of integrated GFP progenitors with antiepileptic activity.

Results: It is more difficult to initiate seizures in mice receiving MGE progenitors. Electrographic seizure events, if observed, are brief in transplanted animals and little or no signs of convulsive behavior are observed. Animals with large numbers of integrated MGE progenitors are most resistant to the development of acute seizure activity.

EXAMPLE 4

MGE Progenitors Reduce Seizure Activity in Mouse Models of Spontaneous Epilepsy

Transplanted MGE progenitor cells are used to enhance synaptic inhibition such that seizure susceptibility is significantly reduced in the host animal. Studies are performed in neocortical tissue sections from wild-type control mice (following grafting) and mouse mutants with known cortical interneuron defects. Three mutants with a demonstrated reduction in synaptic inhibition and hyperexcitability are used: particularly, DIx1-/-, $GAD65^{-/-}$ and $uPAR^{-/-}$. DIx1 mice show generalized electrographic seizures and histological evidence of seizure-induced reorganization and hence display a phenotype comparable to that of human epilepsy associated with interneuron loss. GAD65 mutants appear to have normal numbers of GABAergic cortical interneurons, but a reduced capacity to synthesize GABA (Kash et al., Proc Natl Acad Sci USA. 1997 Dec. 9; 94(25):14060-5). uPAR mutants appear to have a reduced density of GABAergic interneurons in parietal cortex (Powell et al., J. Neurosci. 2003 Jan. 15; 23(2):622-31).

(i) GAD65-/- and uPAR-/- Mice

Hyperexcitable states have been reported in mutants with abnormal cortical interneurons (GAD65 KO) and in mutants with reduced numbers of cortical interneurons (uPAR KO). First, disruption of the GAD65 gene in mice leads to a 50% decrease in cofactor-inducible GAD enzymatic activity (Kash et al., supra). GAD65-deficient mice on a C57Bl/6 background are susceptible to infrequent spontaneous seizures and stress-induced seizures. Second, inactivation of the urokinase plasminogen activator receptor (uPAR) gene in mice leads to a 50-65% reduction in cortical GABAergic interneurons (Powell et al., supra). uPAR KO mice (bred on a C57Bl/6 background) are viable, survive into adulthood, and exhibit overt tonic-clonic seizures or an increased susceptibility to PTZ-induced motor convulsions. Both strains of mutant mice are used. Because background strain can be an important modulator of seizure susceptibility (Schauwecker and Steward, Proc Natl Acad Sci USA. 1997 Apr. 15; 94(8): 4103-8; Schauwecker, Prog Brain Res. 2002; 135:139-48), we are careful to study mutant and wild-type mice bred on only one background strain e.g., the relatively seizure-resistant C57Bl/6.

Following bilateral MGE grafting in $GAD65^{-/-}$ or $uPAR^{-/-}$ mice, and sham operated, strain- and age-matched controls, EEG electrodes are implanted bilaterally in neocortex and monitored with video-EEG. After a 1 wk recovery period, following surgery, animals are monitored each day for 6 hr recording sessions (2 wk monitoring period). In analyzing video-EEG traces the frequency and duration of electrographic seizures recorded are quantified. Behaviors that accompany these discharges are fully characterized by close examination of video-EEG recordings using an investigator blind to the status of the animal; clinician-scientists in the laboratory assist in these studies. The frequency and amplitude of interictal spikes may vary during sleep-wake cycles (Martins da Silva et al. Electroencephalogr Clin Neurophysiol. 1984 July; 58(1):1-13). As such, interictal spikes are always analyzed during periods of non-REM sleep. Because mutant mice can exhibit spontaneous seizure activity (consisting of frequent abnormal slow waves and interictal discharges with associated convulsive behaviors) it is not necessary to induce seizures using kainate or PTZ.

We sacrifice these animals and quantify the number of new GABAergic $GFP^+$ interneurons present in neocortex. We correlate the number of $GFP^+$ cells with seizure severity (as determined from analysis of behavior and EEG). Detailed immunocytochemical studies using antibodies to GAD, NPY, parvalbumin, somatostatin and calbindin are performed. A limited number of slice electrophysiology studies are also performed to analyze sIPSCs in un-treated and grafted animals.

Results: The reduction in functional GABAergic interneurons resulting in a spontaneous epileptic phenotype observed in uPAR KO mice is alleviated by grafting MGE progenitors into these animals. Interictal spikes and behavioral seizures are reduced (or eliminated) in uPAR KO mice receiving MGE grafts. Similar results are observed in GAD65 mutant mice.

(ii) DIx−/− Mice

MGE cells were transplanted into the brains of DIx1−/− mice, a murine model of epilepsy, in a similar manner as described in example 1. For details on DIx1−/− mice, see Cobos et al., Nature Neuroscience, 8:1059-1068, 2005, expressly incorporated herein in its entirety by reference. DIx1 mice show generalized electrographic seizures and histological evidence of seizure-induced reorganization and hence display a phenotype comparable to that of human epilepsy associated with interneuron loss. DIx1 mutant mice transplanted with MGE progenitor cells appeared to have a reduced epilepsy phenotype, measured as a reduction in seizure-like behavior upon handling and a lack of EEG-like seizure activity. Cortical brain slices prepared from DIx mutant mice transplanted with MGE progenitor cells early in development (P0-P2) exhibited a level of inhibition (measured as spontaneous and miniature IPSCs on postsynaptic pyramidal cell targets in regions containing MGE-GFP interneurons) that was comparable to that observed in control DIx heterozygote mice. Specifically, DIx mutants normally showed reduced IPSC frequency and amplitude and these values were "rescued" by MGE transplantation. See FIG. 10. At the whole animal level, DIx mutants normally exhibited handling induced seizures and spontaneous seizures. DIx mutants transplanted with MGE cells did not exhibit handling induced seizures and video-EEG recording confirmed the lack of a seizure phenotype. This demonstrated that MGE cells can be successfully transplanted into the diseased brain and demonstrated reduction or ablation of epileptic symptoms following transplantation.

EXAMPLE 5

MGE Precursors Increase Seizure Latencies and Reduce Mortality in a Rodent Seizure Model A commonly used rodent seizure model (e.g., pilocarpine) was used to investigate the therapeutic potential of MGE-derived interneurons. MGE cells from e13.5 GFP-expressing mice were transplanted into the postnatal (p4) brain using procedures described above. After allowing for migration and integration to occur, single doses of scopolamine followed by pilocarpine (300 mg/kg) were administered to induce acute seizure activity. Mortality and seizure latency were compared among sham-transplanted mice, MGE cell-transplanted recipients, and mice pretreated with phenobarbital (PB), a conventional AED (antiepileptic drug).

Seizure behaviors were scored on a Racine scale by an investigator blind to the status of the animal. It was observed that the transplanted mice and PB-pretreated mice had longer seizure latencies and lower mortality rates compared to sham-transplanted littermates. In grafted mice, seizure protection correlated with the number of newly generated MGE-GFP cells.

Immunohistochemistry and electrophysiology were then carried out as described herein to confirm whether the therapeutic benefit observed in the transplanted mice was due to the inhibitory activity of MGE-derived interneurons. The immunohistochemistry revealed that MGE-derived transplanted cells in the neocortex and hippocampus were mostly neuronal (NeuN+) and GABAergic, as expected. Whole-cell electrophysiological recordings of presynaptic GFP+ cells and postsynaptic pyramidal cells confirmed that transplanted cells were able to functionally integrate and increase synaptic inhibition, as well as receive excitatory inputs from endogenous pyramidal cells.

These results indicate that MGE-derived precursor cells are able to migrate large distances and functionally integrate into existing cortical circuitry, thereby reducing the harmful effects of induced seizures in transplanted mice. These in vivo data provide a strong indication that MGE-derived precursor cells will have therapeutic value in seizure disorders, and other disorders of inhibition, including epilepsy and other disorders described herein.

All references cited are expressly incorporated herein in their entirety by reference.

The invention claimed is:

1. A method of treating a mammal afflicted with a seizure disorder, the method comprising:
   transplanting medial ganglionic eminence (MGE) cells into the central nervous system of a mammal afflicted with a seizure disorder; and
   allowing the transplanted cells to migrate and integrate in the central nervous system of said mammal to form functional inhibitory interneurons that are associated with a reduction in seizure activity in said mammal, thereby treating the seizure disorder in said mammal.

2. The method of claim 1, wherein the MGE cells are transplanted into the brain of said mammal.

3. The method of claim 1, wherein the mammal is selected from the group consisting of mouse, rat, human, livestock animal and domestic animal.

4. The method of claim 1, wherein the MGE cells are transplanted into a region of the central nervous system selected from the group consisting of cerebral cortex, hippocampus, thalamus, and striatum.

5. The method of claim 4, wherein the MGE cells are transplanted into a region of the central nervous system which is free of lesions.

6. The method of claim 1, wherein said transplanting comprises injecting dissociated MGE cells into the central nervous system.

7. The method of claim 6, wherein the MGE cells are injected in association with a carrier.

8. The method of claim 1, wherein the mammal is a human.

9. The method of claim 1, wherein the mammal is an adult.

10. The method of claim 9, wherein the mammal is a human.

11. The method of claim 10, wherein said transplanting comprises injecting dissociated MGE cells into the central nervous system.

12. The method of claim 10, wherein the MGE cells are transplanted into a region of the central nervous system selected from the group consisting of cerebral cortex, hippocampus, thalamus, and striatum.

13. The method of claim 1, wherein said seizure disorder is epilepsy.

14. The method of claim 1, wherein the reduction in seizure activity is measured by electroencephalography (EEG).

15. The method of claim 1, wherein the reduction in seizure activity is measured by analysis of behavior.

16. The method of claim 1, wherein the transplanted MGE cells cause a net increase in inhibitory neuron function in the brain relative to excitatory neuron function.

17. The method of claim 12, wherein said seizure disorder is epilepsy.

18. The method of claim 17, wherein the reduction in seizure activity is measured by electroencephalography (EEG).

19. The method of claim 17, wherein the reduction in seizure activity is measured by analysis of behavior.

* * * * *

UNITED STATES PATENT AND TRADEMARK OFFICE
CERTIFICATE OF CORRECTION

| | | |
|---|---|---|
| PATENT NO. | : 9,192,630 B2 | Page 1 of 1 |
| APPLICATION NO. | : 12/161527 | |
| DATED | : November 24, 2015 | |
| INVENTOR(S) | : Baraban et al. | |

It is certified that error appears in the above-identified patent and that said Letters Patent is hereby corrected as shown below:

In the specification

Please insert at Column 1, line 3 the following:

--GOVERNMENT SUPPORT CLAUSE

This invention was made with government support under grant no. NS048528 awarded by the National Institutes of Health. The government has certain rights in the invention.--

Signed and Sealed this
Twenty-eighth Day of June, 2016

Michelle K. Lee
*Director of the United States Patent and Trademark Office*